(12) United States Patent
Takahashi et al.

(10) Patent No.: US 8,723,946 B2
(45) Date of Patent: May 13, 2014

(54) WORKPIECE INSPECTING APPARATUS AND WORKPIECE INSPECTING METHOD

(75) Inventors: Hisashi Takahashi, Tochigi (JP); Ryo Obara, Tochigi (JP); Koichi Imazu, Tochigi (JP)

(73) Assignee: Honda Motor Co., Ltd., Tokyo (JP)

( * ) Notice: Subject to any disclaimer, the term of this patent is extended or adjusted under 35 U.S.C. 154(b) by 344 days.

(21) Appl. No.: 13/224,955

(22) Filed: Sep. 2, 2011

(65) Prior Publication Data

US 2012/0069173 A1 Mar. 22, 2012

(30) Foreign Application Priority Data

Sep. 16, 2010 (JP) .................................. 2010-207790
Sep. 16, 2010 (JP) .................................. 2010-208332

(51) Int. Cl.
*H04N 9/47* (2006.01)
*G01N 21/88* (2006.01)

(52) U.S. Cl.
CPC .................................. *G01N 21/8806* (2013.01)
USPC ............................................. 348/92; 382/149

(58) Field of Classification Search
USPC ............ 348/92, 125, 129; 382/141, 142, 149, 382/152, 190
See application file for complete search history.

(56) References Cited

U.S. PATENT DOCUMENTS

| | | | | |
|---|---|---|---|---|
| 5,305,391 A | * | 4/1994 | Gomibuchi | 382/142 |
| 6,005,987 A | * | 12/1999 | Nakamura et al. | 382/294 |
| 8,126,259 B2 | * | 2/2012 | Shimura | 382/149 |
| 2005/0259863 A1 | * | 11/2005 | Freifeld | 382/152 |
| 2006/0222233 A1 | * | 10/2006 | Sugihara et al. | 382/144 |

FOREIGN PATENT DOCUMENTS

| | | | |
|---|---|---|---|
| JP | 61-076941 A | | 4/1986 |
| JP | 63-201556 A | | 8/1988 |
| JP | 01-136008 A | | 5/1989 |
| JP | 05-231842 A | | 9/1993 |
| JP | 06-055340 A | | 3/1994 |
| JP | 06-174649 A | | 6/1994 |
| JP | 10-132537 A | | 5/1998 |
| JP | 2006-047040 A | | 2/2006 |
| JP | 2006-047102 A | | 2/2006 |
| JP | 2007-248325 A | | 9/2007 |
| JP | 2009-052917 A | | 3/2009 |
| JP | 2009052917 A | * | 3/2009 |
| JP | 2009-097922 A | | 5/2009 |

OTHER PUBLICATIONS

Naoki, Fuse, Machine translation of patent JP 2009052917 A, Date: Dec. 3, 2009, Translation Date: Oct. 15, 2013.*

* cited by examiner

*Primary Examiner* — Jorge L Ortiz Criado
*Assistant Examiner* — Umber Aggarwal
(74) *Attorney, Agent, or Firm* — Carrier Blackman & Associates, P.C.; Joseph P. Carrier; Jeffrey T. Gedeon

(57) ABSTRACT

A workpiece inspecting apparatus for rotating a workpiece having a shape portion containing a convex portion and a concave portion which are periodically and repetitively formed on the workpiece and picking up images of the shape portion of the workpiece to inspect the workpiece, including a workpiece rotating mechanism that outputs reference pulses at a fixed interval while rotating the workpiece at a fixed rotational speed, an image pickup mechanism that picks up images of the shape portions of the workpiece every image pickup timing based on the reference pulses, an image pickup controller that synchronizes each of the shape portions of the workpiece with the image pickup timing, and an inspection controller that executes image processing of taking a difference between a pickup k-th (k represents an integer) image and a pickup (k+1)-th image and detects a defect on the basis of differential data representing the difference.

11 Claims, 14 Drawing Sheets

FIG. 13
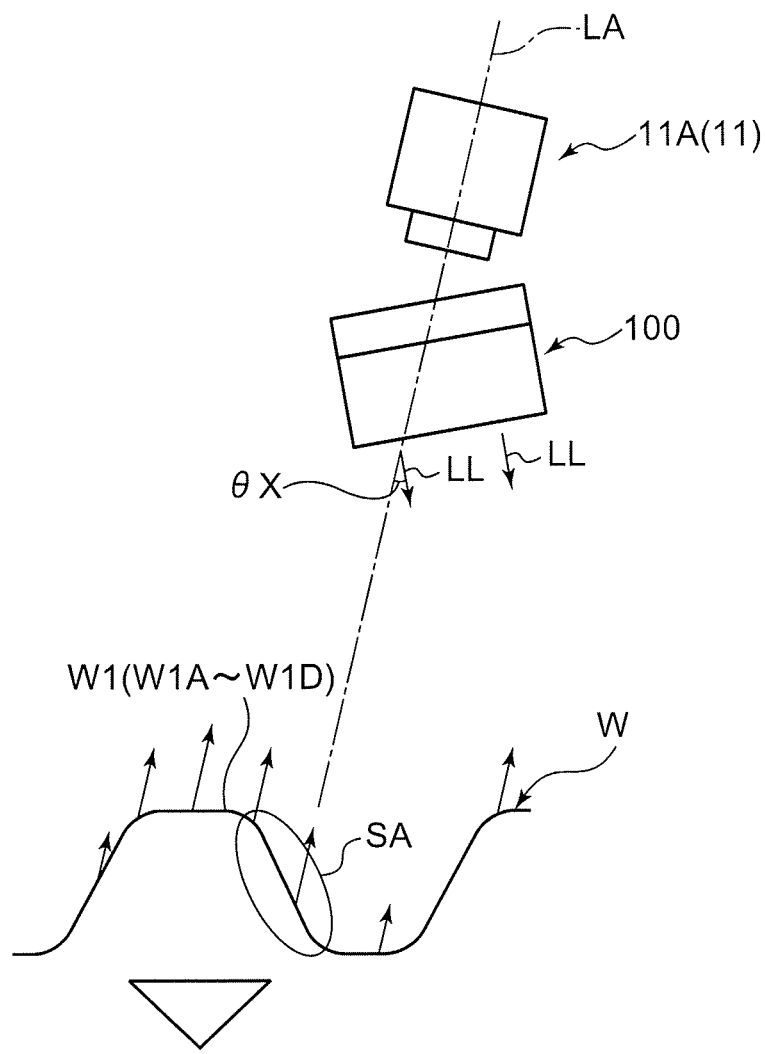
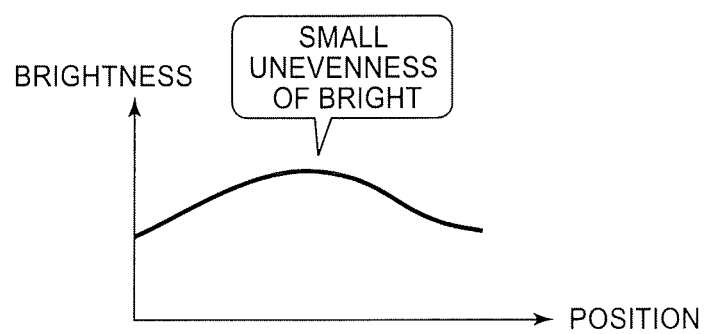

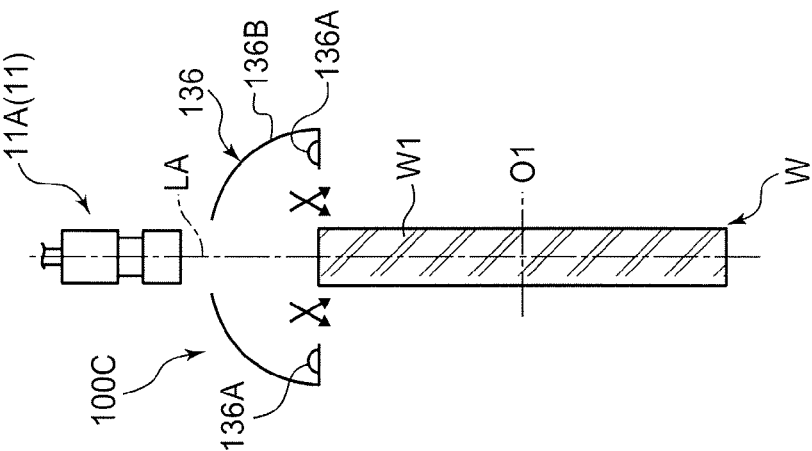
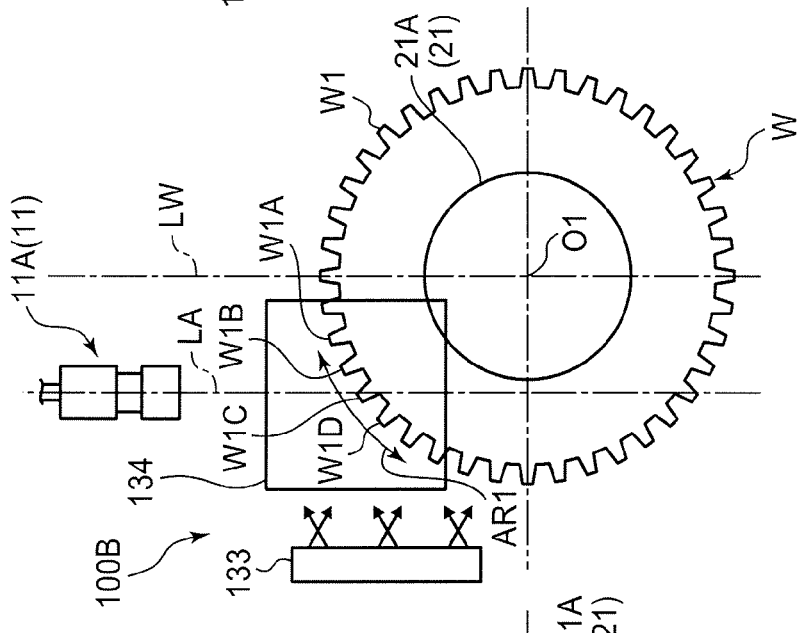
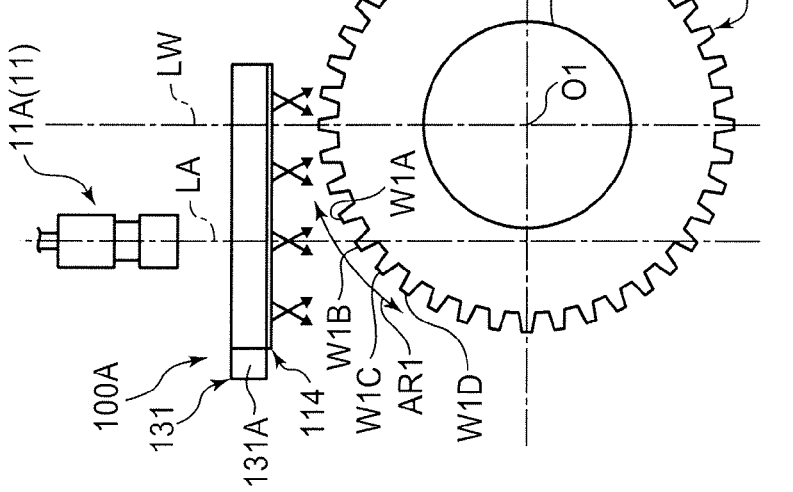

WORKPIECE INSPECTING APPARATUS AND WORKPIECE INSPECTING METHOD

INCORPORATION BY REFERENCE

The present application claims priority under 35 U.S.C. §119 to Japanese Patent Application No. 2010-207790 filed on Sep. 16, 2010 and Japanese Patent Application No. 2010-208332 filed on Sep. 16, 2010. The content of the applications is incorporated herein by reference in its entirety.

BACKGROUND OF THE INVENTION

1. Field of the Invention

The present invention relates to a workpiece inspecting apparatus and a workpiece inspecting method for rotating a workpiece having a shape portion containing projecting portions and recess portions which are repetitively formed on the workpiece, picking up images of the shape portion of the workpiece and inspecting the workpiece on the basis of the pickup images.

2. Description of the Related Art

There is known an appearance inspecting apparatus with which images of a gear wheel as a workpiece fed by a feeding unit are picked up by a camera and the presence or absence of a defect in gear teeth of the gearwheel is detected on the basis of the pickup images (for example, see JP-A-05-231842). According to this type of appearance inspecting apparatus, an impeller (turbine wheel) used for a turbocharger of an engine for a vehicle or the like is supported by a servo motor so that it is freely rotatable, step feeding is executed on the turbine wheel by the servo motor, and the rotation of the turbo wheel is stopped at an image pickup position, thereby allowing image pickup of all the vanes of the turbine wheel by a fixedly installed camera (for example, see JP-A-2009-52917).

When images of a portion which is periodically and repetitively formed on a workpiece (for example, teeth of a gear wheel, vanes of an impeller (turbine wheel) or the like) are picked up and an appearance inspection is executed on the basis of each pickup image, it is desired to pick up respective images under the same condition (for example, pick up the images at the same position).

As compared with the technique disclosed in JP-A-05-231842, the technique disclosed in JP-A-2009-52917 has a more excellent advantage that images of many places to be inspected can be picked up by rotating the turbine wheel. However, this technique step-feeds and stops the workpiece at a predetermined rotation angle, and thus needs a mechanism and a control operation for stopping the workpiece with high precision. Furthermore, the workpiece is stopped every time an image is picked up, and thus much time is required until pickup of all imaged has been completed. Still furthermore, a processing load imposed on image processing for detecting a damage or a continuous defect on the basis of pickup images is large, and thus this also causes increase of the processing time.

Furthermore, according to the above techniques, images of a workpiece are picked up under illumination in a fixed direction or from an observation point in a fixed direction, and thus a damage or the like on the workpiece may be overlooked.

SUMMARY OF THE INVENTION

The present invention has been implemented in view of the foregoing situation, and has an object to provide a workpiece inspecting apparatus and a workpiece inspecting method that can shorten a time required for image pickup and inspection of a workpiece having a shape portion which is periodically and repetitively formed.

In order to attain the above object, according to an aspect of the present invention, a workpiece inspecting apparatus for rotating a workpiece having a shape portion containing a convex portion and a concave portion which are periodically and repetitively formed on the workpiece and picking up images of the shape portion of the workpiece to inspect the workpiece, comprises: a workpiece rotating mechanism that outputs reference pulses at a fixed interval while rotating the workpiece at a fixed rotational speed; an image pickup mechanism that picks up images of the shape portions of the workpiece every image pickup timing based on the reference pulses; an image pickup controller that synchronizes each of the shape portions of the workpiece with the image pickup timing; and an inspection controller that executes image processing of taking a difference between a pickup k-th (k represents an integer) image and a pickup (k+1)-th image and detects a defect on the basis of differential data representing the difference.

According to this construction, the shape portion of the workpiece and the image pickup timing are synchronized with each other on the basis of the reference pulses, the image processing of taking the difference between the pickup k-th image (k represents an integer) and the pickup (k+1)-th image is executed, and a defect is detected on the basis of the thus-obtained differential data. Accordingly, images can be picked up with stopping the rotation of the workpiece (non-stop image pickup), and thus the time required for image pickup can be shortened. Furthermore, the amount of target data for defect determination can be reduced in the defect detection based on the differential data between the sequential images as compared with the defect detection based on the data of a single pickup image, and thus the time required for workpiece inspection can be shortened. Accordingly, the total time required for the image pickup and the inspection of the workpiece having the shape portion periodically and repetitively formed on the workpiece can be shortened.

In the above construction, the image pickup mechanism picks up the images of the shape portions every fixed period based on the reference pulses so that the shape portions at least two places are contained in each of the pickup images, and has an illuminating device that illuminates light obliquely to the shape portions as references within a predetermined image pickup area when the image pickup mechanism performs image pickup.

According to this construction, the image pickup is performed every fixed period based on the reference pulses output at a fixed interval so that at least two or more shape portions of the workpiece are contained in each image while the workpiece is rotated at a fixed rotational speed, and a defect is detected on the basis of the differential data between a picked up k-image (k represents an integer) and a pickup (k+1)-th image. Furthermore, the illuminating device for obliquely illuminating light to the shape portions as references within the image pickup area is provided. Accordingly, the image pickup can be performed without stopping the rotation of the workpiece (non-stop image pickup) while the unevenness of brightness is reduced by the illuminating device, and thus the time required for the image pickup can be shortened. In addition, as compared with the case where a defect is detected on the basis of the data of a single pickup image, the amount of target data used to determine a defect can be more greatly reduced in the defect detection based on the differential data between sequential (adjacent) pickup images, and thus the time required for the inspection of the workpiece can be also shortened. Accordingly, the total time required for the image pickup and the inspection of a workpiece having periodically and repetitively formed shape portions can be shortened, and overlooking of a defect can be suppressed.

In the above construction, the workpiece is designed to be substantially circular in plan view and have the shape portions that are periodically and repetitively formed along a peripheral direction of the workpiece on the workpiece, and the illuminating device illuminates light obliquely to the shape portions as the references within the image pickup area in plan view.

According to this construction, the evenness of brightness of the shape portions, etc. can be reduced while light is applied to the overall surface when viewed from the image pickup mechanism side, and the overlooking of a defect can be more greatly suppressed. Furthermore, the image pickup can be performed on each shape portion of the workpiece under different illumination environments for each shape portion, and this also enhances the defect detection precision and suppresses overlooking of a defect.

In the above construction, the illuminating device has a transmission type diffuser panel for converting the light to diffusion light and applying the diffusion light to the image pickup area. According to this construction, the unevenness of brightness in the pickup image can be more greatly reduced, and the overlooking of a defect can be also more greatly prevented.

In the above construction, the illuminating device has an optical path portion through which light is passed to the image pickup area of the image pickup area, an optical axis of the optical path portion is oblique to the shape portions as the references within the image pickup area, and the diffuser panel is provided at a light emission side of the optical path portion. According to this construction, by adjusting the position and direction of the optical path portion, the inspecting apparatus can be easily adjusted so that the unevenness of brightness of the shape portions as references can be reduced.

In this case, the optical axis of the optical path portion is set to be oblique to the lens optical axis of the image pickup mechanism, whereby the unevenness of brightness in the pickup image can be more efficiently reduced.

In the above construction, a lens optical axis of the image pickup mechanism is offset parallel from a workpiece center passing axis that passes through a rotational center of the workpiece and extends in a radial direction of the workpiece in plan view, an illumination center of the illuminating device is disposed at an opposite side to the workpiece center passing axis with respect to the lens optical axis in plan view, and the illuminating device is tilted with the illumination center set at the center so that a light emission side of the illuminating device faces a rotational center side of the workpiece W. according to this construction, when image pickup is performed on plural shape portions, occurrence of shadow caused by the shape portions can be prevented.

In the above construction, the inspecting processor executes another image processing of obtaining the difference between a pickup image and a pre-stored image of a good product, and executes another inspection processing of detecting a defect on the basis of data of the difference obtained in the other image processing. According to this construction, defects which are continuously connected to one another over plural shape portions can be detected with high precision.

Furthermore, in the above construction, the inspecting processor determines the workpiece as a good product when no defect is detected in each of the differential data between the pickup k-th image and the pickup (k+1)-th image and the differential data obtained in the other image processing. According to this construction, a good product can be determined with high precision.

In the above construction, the image pickup mechanism comprises: a workpiece pulse output mechanism equipped with a rotator that is rotated integrally with the workpiece and has detection target portions arranged at the same angular interval as the shape portions of the workpiece with respect to a rotational center of the rotator, and a proximity sensor that outputs a workpiece pulse every time each of the detection target portions of the rotator is detected, and a pulse counter that counts an interval between the workpiece pulses on the basis of the reference pulses and achieves a pulse number corresponding to the interval, and the image pickup controller performs image pickup at the image pickup timing based on the reference pulses by using the workpiece pulse as a trigger, and performs image pickup at the image pickup timing based on the reference pulses every time the reference pulses whose number corresponds to the pulse number are output from the image pickup timing.

According to the above construction, the image pickup can be performed on the basis of the reference pulses while matching the image pickup timing with the actual shape portions of the workpiece. Therefore, images of the respective shape portions can be picked up under the same condition (at the same position) with high precision. By the enhancement of the image pickup precision, the defect detection precision can be enhanced, and the workpiece can be rotated at high speed with keeping this detection precision. Therefore, the inspecting time can be further shortened.

Furthermore, according to another aspect of the present invention, a workpiece inspecting method for rotating a workpiece having a shape portion containing a convex portion and a concave portion periodically and repetitively formed on the workpiece and picking up images of the shape portions of the workpiece, comprises: an image pickup step that synchronizes the shape portions of the workpiece with an image pickup timing of an image pickup mechanism for picking up images of the shape portions of the workpiece on the basis of the reference pulses from a workpiece rotating mechanism for outputting reference pulses at a fixed interval while rotating the workpiece at a fixed rotational speed; and an inspection processing step that executes image processing of achieving the difference between a pickup k (k represents an integer) image and a pickup (k+1)-th image and detects a defect on the basis of the data of the difference.

In the above method, when the image pickup mechanism performs image pickup, the image pickup is performed so that the shape portions of at least two places (i.e., at least two or more shape portions) are contained in each image, and the respective shape portions are different from each other in luminosity.

According to the above method, an image of plural shape portions under different luminosities is picked up, and thus for each shape portion, plural images under plural illumination environments having different luminosities can be picked up. By inspecting each pickup image, plural inspecting timings can be set. Therefore, the time for the image pickup and the inspection of the workpiece having shape portions which are periodically and repetitively formed on the workpiece can be shortened, and overlooking of a defect can be prevented.

According to the present invention, the shape portion of the workpiece and the image pickup timing are synchronized with each other on the basis of the reference pulses, the image processing of taking the difference between the pickup k-th image (k represents an integer) and the pickup (k+1)-th image is executed, and a defect is detected on the basis of the thus-obtained differential data. Therefore, the time for the image pickup and the inspection of the workpiece having shape portions which are periodically and repetitively formed on the workpiece can be shortened.

Furthermore, the image pickup mechanism picks up the images of the shape portions every fixed period based on the reference pulses so that the shape portions at least two places are contained in each of the pickup images, and has an illuminating device that illuminates light obliquely to the shape portions as references within a predetermined image pickup area when the image pickup mechanism performs image pickup. Therefore, the time for the image pickup and the inspection of the workpiece having shape portions which are periodically and repetitively formed on the workpiece can be shortened, and overlooking of a defect can be prevented.

BRIEF DESCRIPTION OF THE DRAWINGS

FIG. 13 is a diagram showing a case where the optical axis of illumination light is inclined with respect to the lens optical axis;
and
FIGS. 14A to 14C are diagrams showing comparison examples.

DETAILED DESCRIPTION OF THE EMBODIMENT

An embodiment according to the present invention will be described with reference to the drawings.

Figure 1:
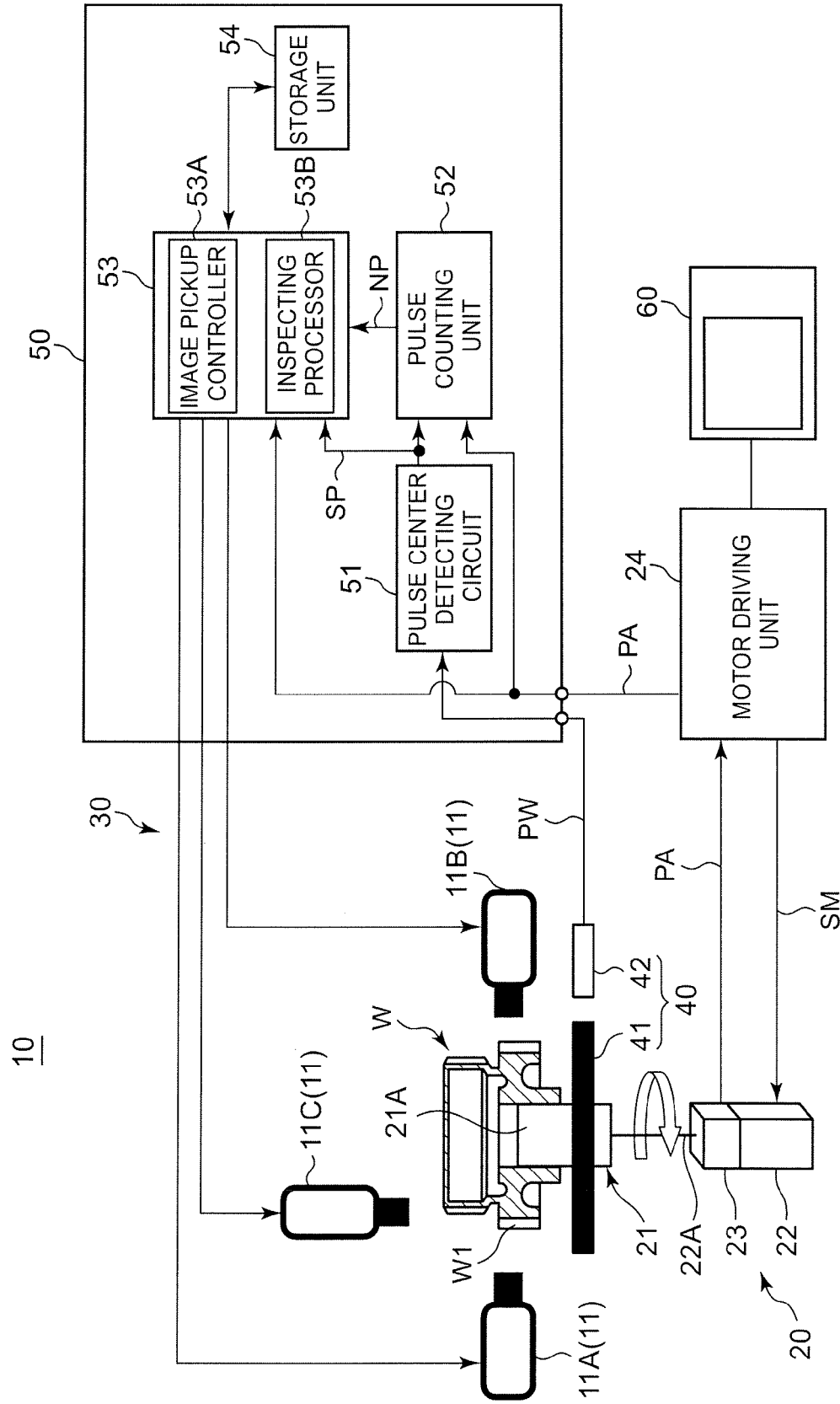
FIG. 1 is a diagram showing a workpiece inspecting apparatus according to a first embodiment of the present invention.

FIG. 1 is a diagram showing a workpiece inspecting apparatus according to an embodiment of the present invention.

Figure 2:
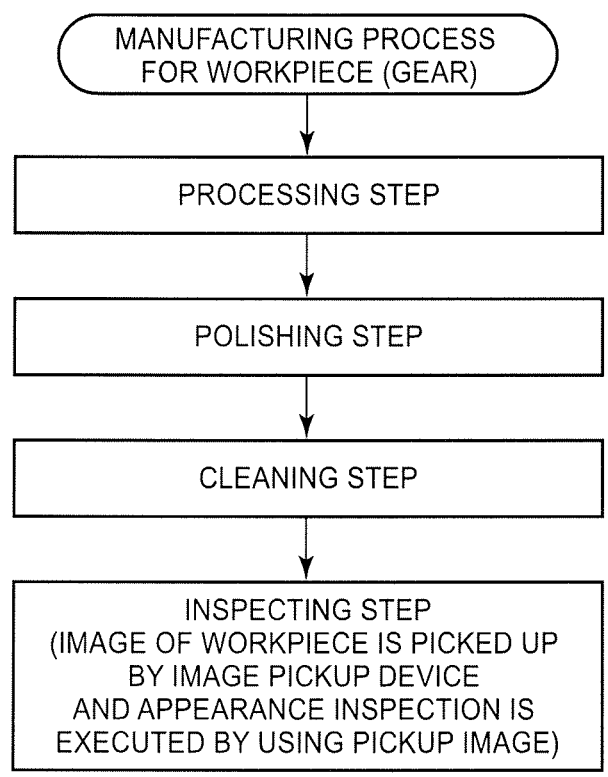
FIG. 2 is a diagram showing a process of manufacturing a workpiece.

The workpiece inspecting apparatus 10 also serves as an image pickup device for appearance inspection, and is disposed in a process of manufacturing a workpiece (a gearwheel in this embodiment) W. This device picks up images of the workpiece W manufactured in the manufacturing process by using a camera (image pickup unit) 11 to obtain the images suitable for appearance inspection, and executes inspection processing (image processing) on these images. Here, the manufacturing process for the workpiece W as shown in FIG. 2 progresses like processing step of workpiece W (gear cutting, etc. of a gear wheel)→grinding step→cleaning step→inspecting step, and the workpiece inspecting apparatus 10 is used in the inspecting step as a final step.

More specifically, after the workpiece W is subjected to the grinding step, a worker changes the setting to shift the workpiece W to the cleaning step. After the workpiece W is subjected to the cleaning step, cleaning liquid is removed from the workpiece W by air blow, and then the workpiece W is shifted to the inspecting step containing image pickup processing in the workpiece inspecting apparatus 10 while the setting (setup state) of the cleaning step is kept. That is, the cleaning step and the inspecting step are executed under the same setting, whereby the time required for the process is shortened.

As shown in FIG. 1, this workpiece inspecting apparatus 10 has a workpiece rotating mechanism 20 for rotating a workpiece W, an image pickup mechanism 30 for picking up images of the workpiece W being rotated, a pulse output mechanism (workpiece pulse output mechanism) 40 for outputting a workpiece pulse PW representing the position of a tooth portion W1 (described later with reference to FIG. 3) which is periodically and repetitively formed on the workpiece W, an information processing device 50 for controlling the above units and executing various kinds of information processing, and an operating device 60 having a display function which is operated by a worker. The information processing device 50 is constructed by installing a mount board having various kinds of circuits formed thereon into a personal computer.

The workpiece rotating mechanism 20 has a holder portion 21 to which the workpiece W is fixed, a motor 22 for rotationally driving the holder portion 21, an encoder 23 which is disposed on the rotational shaft 22A of the motor 22, and a motor driving unit 24.

The holder portion 21 is connected to the rotational shaft 22A of the motor 22 and rotated at the same speed as the rotational shaft 22A, thereby rotating the workpiece W. This holder portion 21 has a shaft portion 21A inserted in a through hole which penetrates through the workpiece W in the axial direction thereof, and a publicly known clamp mechanism (not shown) for claiming the workpiece W concentrically with the shaft portion 21A, and the shaft portion 21A is joined to the workpiece W by a key K (see FIG. 3), whereby the shaft portion 21A and the workpiece W are key-joined to each other so as to rotate integrally with each other. The workpiece W of this embodiment is a metal gear wheel used for a transmission of a vehicle, and a key groove is formed on this type of gear wheel. The workpiece W is fixed to the holder portion 21 by using this key groove.

A shown in FIG. 1, a workpiece detecting jig (rotator) 41 constituting a part of the pulse output mechanism 40 is secured to a base end side of the shaft portion 21A (the rotational shaft 22A side of the motor 22).

Figure 3:
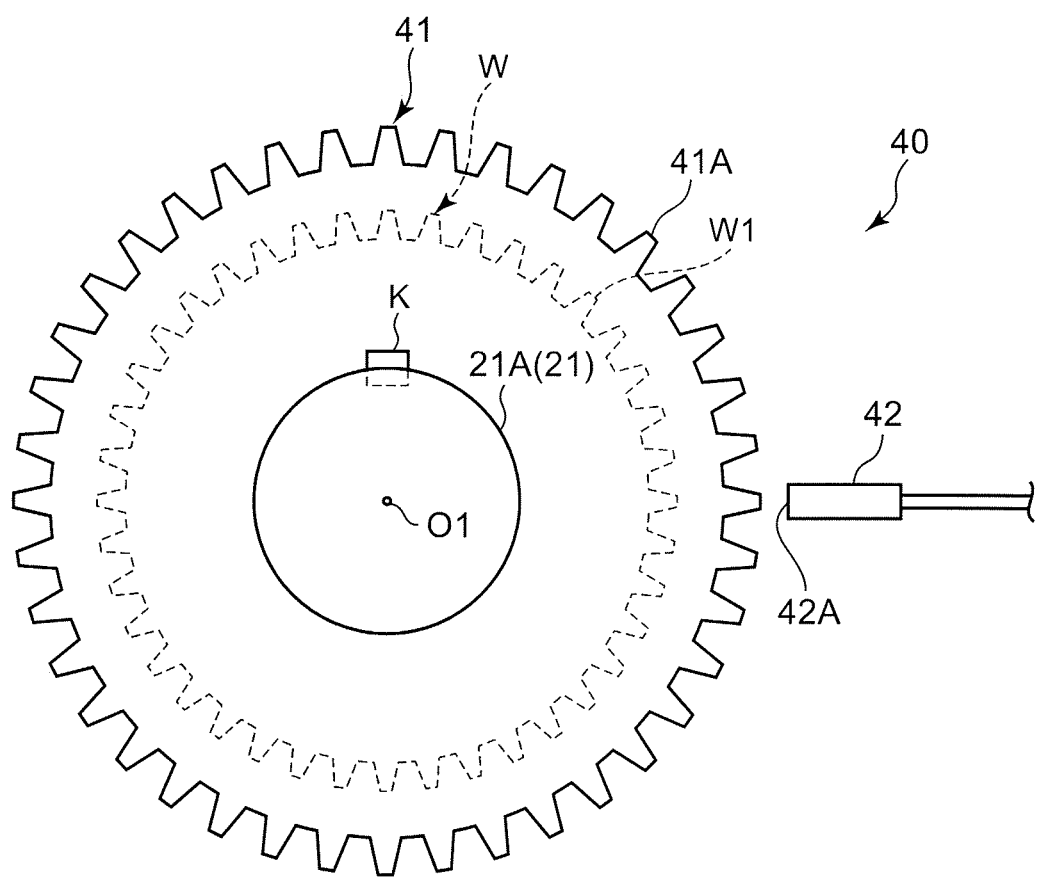
FIG. 3 is a diagram showing a workpiece detecting jig together with a peripheral construction thereof.

FIG. 3 is a diagram showing the workpiece detecting jig 41 together with the peripheral construction thereof.

The workpiece detecting jig 41 is a plate-like member which imitates the workpiece W fixed to the holder portion 21, and the workpiece detecting jig 41 has such a shape that a pseudo tooth portion (pseudo shape portion, detection target portion) 41A which is periodically and repetitively formed on the workpiece detecting jig 41 can be detected by a proximity sensor 42.

More specifically, this workpiece detecting jig 41 is a diameter-increasing part which increases in diameter from the shaft portion 21A with the rotational center O1 of the shaft portion 21A at the center. The workpiece detecting jig 41 is designed as a thin plate having pseudo tooth portions (detection target portions) 41A formed by projecting portions which protrude outwardly in the radial direction and are arranged at an angular interval equal to the pitch of the tooth portions W1 of the workpiece W. In other words, the workpiece detecting jig 41 is designed like a spur wheel whose cross-sectional shape has a similar figure to the side cross-sectional shape of the workpiece W.

The workpiece detecting jig 41 is joined to the shaft portion 21A through a key so as to be rotated integrally with the shaft portion 21A in the neighborhood of the back surface of the workpiece W. Therefore, the workpiece detecting jig 41 functions as a rotator rotating integrally with the workpiece W at a position which is displaced from the workpiece W in the axial direction, but in the neighborhood of the workpiece W.

Furthermore, the pseudo tooth portions 41A of the workpiece detecting jig 41 and the tooth portions W1 of the workpiece W are arranged at the same angular interval with respect to the rotational center O1 of the shaft portion 21A. In this construction, the workpiece detecting jig 41 and the workpiece W are joined to each other through the key K as shown in FIG. 3, whereby the pseudo tooth portion 41A of the workpiece detecting jig 41 and the tooth portion W1 of the workpiece W are aligned with each other in phase.

Furthermore, as shown in the figures, the workpiece detecting jig 41 is formed as a thin plate member, and thus the workpiece detecting jig 41 can be easily disposed by using a base-end side area of the holder portion 21 in which the workpiece W is not mounted.

A servo motor suitable for speed control is used as the motor 22, and under the control of the information processing device 50, the motor 22 is rotationally driven at a fixed rotational speed on the basis of a motor driving signal SM output from the motor driving unit 24.

The encoder 23 is disposed on the rotational shaft 22A of the motor 22, and outputs reference pulses PA whose frequency corresponds to the rotational speed of the rotational shaft 22A. In this construction, the motor 22 is driven at a fixed rotational speed, and thus the encoder 23 outputs reference pulses PA having a fixed frequency.

An encoder for outputting pulses whose number is ten to one hundred times as large as the number of workpiece pulses PW output at the positions of the tooth portions W1 of the workpiece W within the same time is used as the encoder 23, that is, the resolution of the encoder 23 is set so that ten to one hundred pulses (for example, 16 pulses) are output at the rotational angle corresponding to one pitch of the tooth portions W1 of the workpiece W. A rotary encoder is used as the encoder 23.

The reference pulses PA output from the encoder 23 are input to the motor driving unit 24. The motor driving unit 24 executes feed-back control on the motor 22 on the basis of the reference pulses PA to control the rotational speed of the motor 22 to a fixed rotational speed with high precision. Furthermore, the reference pulses PA are also input to the information processing device 50 through the motor driving unit 24.

The motor driving unit 24 is constructed by PLC (Programmable Logic Controller) having a motor control function. However, the present invention is not limited to this style, and the motor driving unit 24 may be contained in the information processing device 50.

An operating device 60 having a display function is connected to the motor driving unit 24, and a worker's operation instruction is input to the motor driving unit 24 by operating an operation panel provided to the operating device 60, and the motor driving unit 24 and the information processing device 50 execute various kinds of processing according to the operation instruction concerned. Furthermore, the operating device 60 having the display function has a display unit for displaying each kind of information input through the motor driving unit 24.

The pulse output mechanism 40 has the workpiece detecting jig 41 described above, and a single proximity sensor 42 for detecting the pseudo tooth portions 41A of the workpiece detecting jig 41 in a contactless style. As shown in FIG. 3, the proximity sensor 42 is configured so that a sensor unit 42A is disposed so as to face the outer peripheral surface of the workpiece detecting jig 41 and outputs a workpiece pulse PW every time each pseudo tooth portion 41A of the workpiece detecting jig 41 is magnetically detected.

As shown in FIG. 1, the workpiece pulse PW is input to a pulse center detecting circuit 51 in the information processing device 50, and center data SP representing the center of the workpiece pulse PW (corresponding to the pulse width center) is generated by the pulse center detecting circuit 51 and input to a pulse counter 52 and a controller 53 (an image pickup controller 53A and an inspecting processor 53B) in the information processing device 50.

The pulse counter 52 counts the pulse number NI (called as a reference pulse number NP) of the reference pulses PA between the centers of continuous workpiece pulses PW to obtain the reference pulse number NP between the workpiece pulses PW, and notifies the reference pulse number NP to the controller 53.

The controller 53 functions as an image pickup controller 53A for controlling the operation of the camera 11 so as to pickup images at the imaging timings based on the reference pulses PA. The reference pulses PA are input to the controller 53, and the center of the workpiece pulse PW detected by the pulse center detecting circuit 51 and the reference pulse number NP between the workpiece pulse PW which is counted by the pulse counter 52 are notified to the controller 53.

The controller 53 is connected to a workpiece image pickup camera 11 through a wire to transmit an image pickup instruction to the camera 11 and also obtain image data picked up by the camera 11.

In the figures, reference numeral 54 represents a storage unit for storing workpiece information such as the image pickup data, the reference pulse number NP, the number of teeth of the workpiece W (the number of shape portions), etc. A computer-readable recording medium such as a magnetic recording medium, an optical recording medium, a semiconductor recording medium or the like is applied as the storage unit 54.

The information processing device 50 and the camera 11 constitute an image pickup mechanism 30. In this embodiment, plural cameras (three cameras in this embodiment) are fixedly installed as the camera 11 to pick up images of the tooth portions W1 of the workpiece W under different conditions.

Specifically, as shown in FIG. 1, these cameras 11 contain a tooth face image pickup camera for picking up an image of a tooth face (the overall surface of the tooth portion W1) (first image pickup unit) 11A, a tooth tip image pickup camera for picking up an image of a tooth tip (the tip of the tooth portion W1) (second image pickup unit) 11B, and an end face image pickup camera for picking up an image of a tooth face (the tooth portion W1) (third image pickup unit) 11C.

Digital cameras for picking up still images are used as these cameras 11, and have shutter speed performance with which pickup images are not blurred even when the images of the workpiece W being rotated are picked up, a sufficient number of pixels for appearance inspection, and a lens suitable for image pickup of each part. A so-called area camera (which is also called as an area sensor camera) is used as the tooth face image pickup camera 11A, and so-called line cameras (which are also called as line sensor cameras) are used as the tooth tip image pickup camera 11B and the end face image pickup camera 11C.

Figure 4:
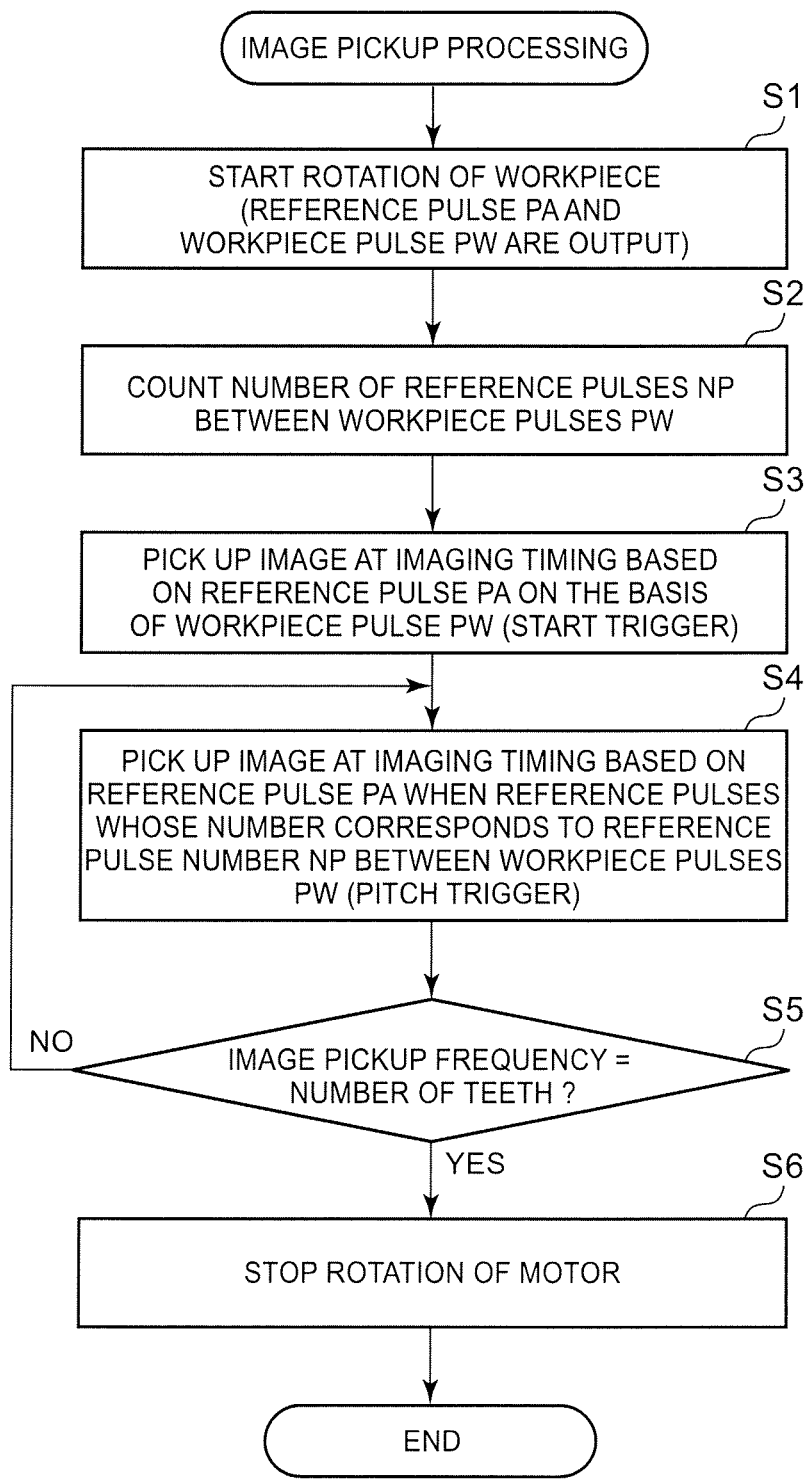
FIG. 4 is a flowchart showing the operation of the workpiece inspecting apparatus.

Next, the operation when the workpiece inspecting apparatus 10 controls the image pickup of the tooth face image pickup camera 11A will be described. FIG. 4 is a flowchart showing this operation.

First, the workpiece inspecting apparatus 10 starts the rotating operation of the motor 22 by the motor driving unit 24 (step S1: start of rotation step). In this case, the motor 22 is controlled to rotate at a preset fixed rotational speed.

When the motor 22 is driven to rotate, the reference pulses PA are output from the encoder 23, and also the workpiece pulses PW are output from the proximity sensor 42 (workpiece pulse output step).

Figure 5:
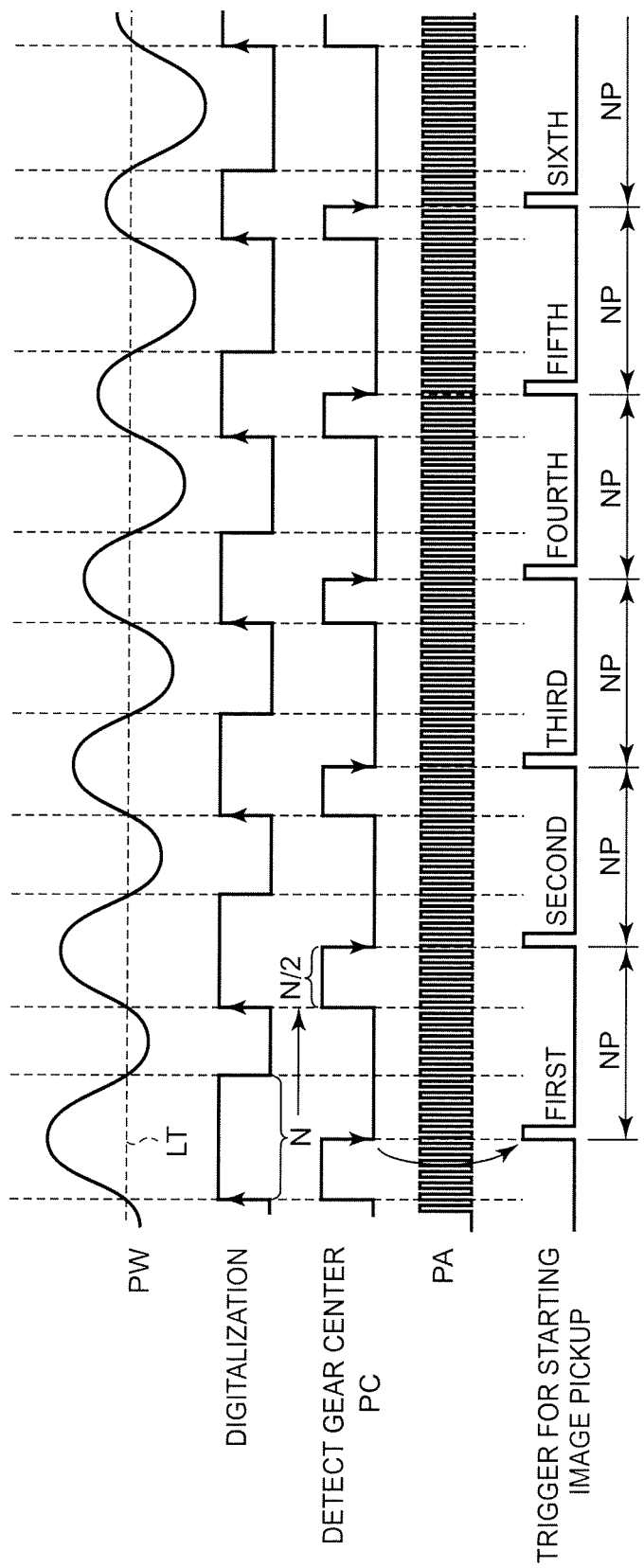
FIG. 5 is a time chart of output of pulses.

The pulse outputs from the encoder 23 and the proximity sensor 42 are obtained as a time chart shown in FIG. 5. As shown in FIG. 5, the proximity sensor 42 generates an output signal voltage having a peak at the center portion thereof (i.e., high-crowned output signal voltage) in the range of a single tooth portion (shape portion) which is periodically and repetitively formed on the workpiece W, and this output signal voltage is digitalized. In FIG. 5, reference character LT represents a threshold level when the workpiece pulses PW are digitalized. The pulse center detecting circuit 51 measures the digitalized pulse width N, generates a half pulse width (N/2) of the measured pulse width N in synchronism with a next pulse rising through an output signal voltage from the proximity sensor 42.

Accordingly, the end edge of the pulse of the generated pulse width (N/2) corresponds to the center position of the tooth portion W1. Therefore, the pulse number of the reference pulses PA is counted in conformity with the digitalized pulse width N, and the pulse width of the half pulse width (N/2) of this count value is generated, whereby the center of the workpiece pulse PW (the pulse width center), that is, the tooth portion center of the workpiece W is detected.

Furthermore, during this rotation, the reference pulse number NP between the workpiece pulses PW is counted by the pulse counter 52 (step S2: pulse count step), and the processing of the step S3 and subsequent steps (image pickup step) is executed.

In this case, the controller 53 detects the image pickup timing based on the reference pulse PA by using the workpiece pulse PW as a trigger for starting image pickup (start trigger), and outputs an image pickup trigger signal to the tooth face image pickup camera 11A at this image pickup timing, thereby making the tooth face image pickup camera 11A pick up an image.

At this time, the controller 53 specifies from the reference pulse PA the image pickup timing corresponding to the center of the workpiece pulse PW detected by the pulse center detecting circuit 51, and performs the image pickup operation at this specified timing. Therefore, the image pickup can be accurately performed at the timing at which the proximity sensor 42 detects the tooth portion center of the workpiece W. The controller 53 of this embodiment is configured so that any one of the falling edge and rising edge of the reference pulse PA may be selected and used as an image pickup timing (start trigger).

In this embodiment, for a first image pickup operation, the tooth tip center detection pulse PC is set as a trigger for starting image pickup. That is, the image pickup timing is not specified from the reference pulses PA, but the timing of the end edge of the tooth tip center detection pulse PC itself is set as the image pickup timing. Accordingly, the error between the image pickup timing and the timing at which the tooth portion center of the workpiece W is detected by the proximity sensor 42 is minimized.

Subsequently, the controller 53 determines on the basis of the image pickup timing whether only the reference pulses PA whose number corresponds to the reference pulse number NP are output, and outputs the image pickup trigger signal to the tooth face image pickup camera 11A every time the reference pulse number NP of reference pulses PA are output, thereby making the tooth face image pickup camera 11A pick up an image (step S4).

In this case, the controller 53 counts an image pickup frequency, and determines whether the counted image pickup frequency is coincident with the number of teeth of the workpiece W. When they are not coincident with each other (step S5: NO), the image pickup processing of the step S4 is executed again. When the counted image pickup frequency is coincident with the number of teeth (step S5: YES), the rotation of the motor 22 is stopped (step S6), and the image pickup processing is finished.

That is, with respect to the second and subsequent image pickup operations, the image pickup trigger signal is output to the tooth face image pickup camera 11A on the basis of the reference pulses PA from the encoder 23, whereby image pickup can be precisely performed at a fixed interval. According to this embodiment, the image pickup timing for the first image pickup is not specified from the reference pulse PA. However, the present invention is not limited to this style, and the image pickup timing may be also specified from the reference pulses PA for the first image pickup.

As described above, the image pickup operation is carried out at the interval of the workpiece pulses PW, and thus the image pickup operation can be executed in synchronism with the tooth portion (shape portion) W1 of the actual workpiece W. Accordingly, images of the toot faces corresponding to the contours of the same tooth portions W1 are continuously picked up in the visual field of the tooth face image pickup camera 11A, and thus images of the respective tooth portions W1 which are picked up under the same condition (at the same position) can be obtained. Here, installation of the tooth face image pickup camera 11A is installed and the camera setting (selection of a lens, magnification, etc.) are performed so that an image containing tooth portions W1 at two or more places can be picked up.

In addition, the image pickup frequency is set to the number of the teeth of the workpiece W, and thus when all the tooth portions W1 are subjected to image pickup at the same position, the image pickup operation can be automatically finished. Furthermore, with respect to the first image pickup operation, the image pickup operation is executed by using, as a trigger, the tooth tip center detection pulse PC generated on the basis of the workpiece pulse PW, and with respect to the second and subsequent image pickup operations, the image pickup operations are executed at a fixed interval by using the reference pulse PA from the encoder 23 as a trigger. Therefore, the error of the image pickup timing can be reduced The fine adjustment of the image pickup position of each tooth portion W1 can be performed by fine adjustment of the position of the tooth face image pickup camera 11A or by correcting the output timing of the image pickup trigger signal by only a minute time.

The data of these pickup images are accumulated in the storage unit 54 provided to the information processing device 50, and the presence or absence of a defect is determined by a defect detecting function based on image processing which is provided to the information processing device 50. The determination result is notified to the external through the information processing device 50 and the operating device 60 having the display function.

In this embodiment, the controller 53 functions not only as the image pickup controller 53A for controlling image pickup, but also as the inspecting processor 53B for executing the defect detection processing (defect detecting step). This controller 53 executes defect detection processing based on adjacent tooth difference for obtaining differential data between sequential pickup images which are sequentially picked up (that is, the differential data between the image data of respective adjacent teeth, and this differential data will be hereinafter referred to as adjacent tooth differential data) and detecting a defect on the basis of the differential data concerned (hereinafter referred to as first defect detection processing), and also executes defect detection processing based on non-defective tooth difference for obtaining differential data between a pickup image and an image of a non-defective product (this differential data will be hereinafter referred to as non-defect differential data) and detect a defect on the basis of the differential data concerned (hereinafter referred to as second defect detection processing). The defect detection processing will be described hereunder.

Figure 6:
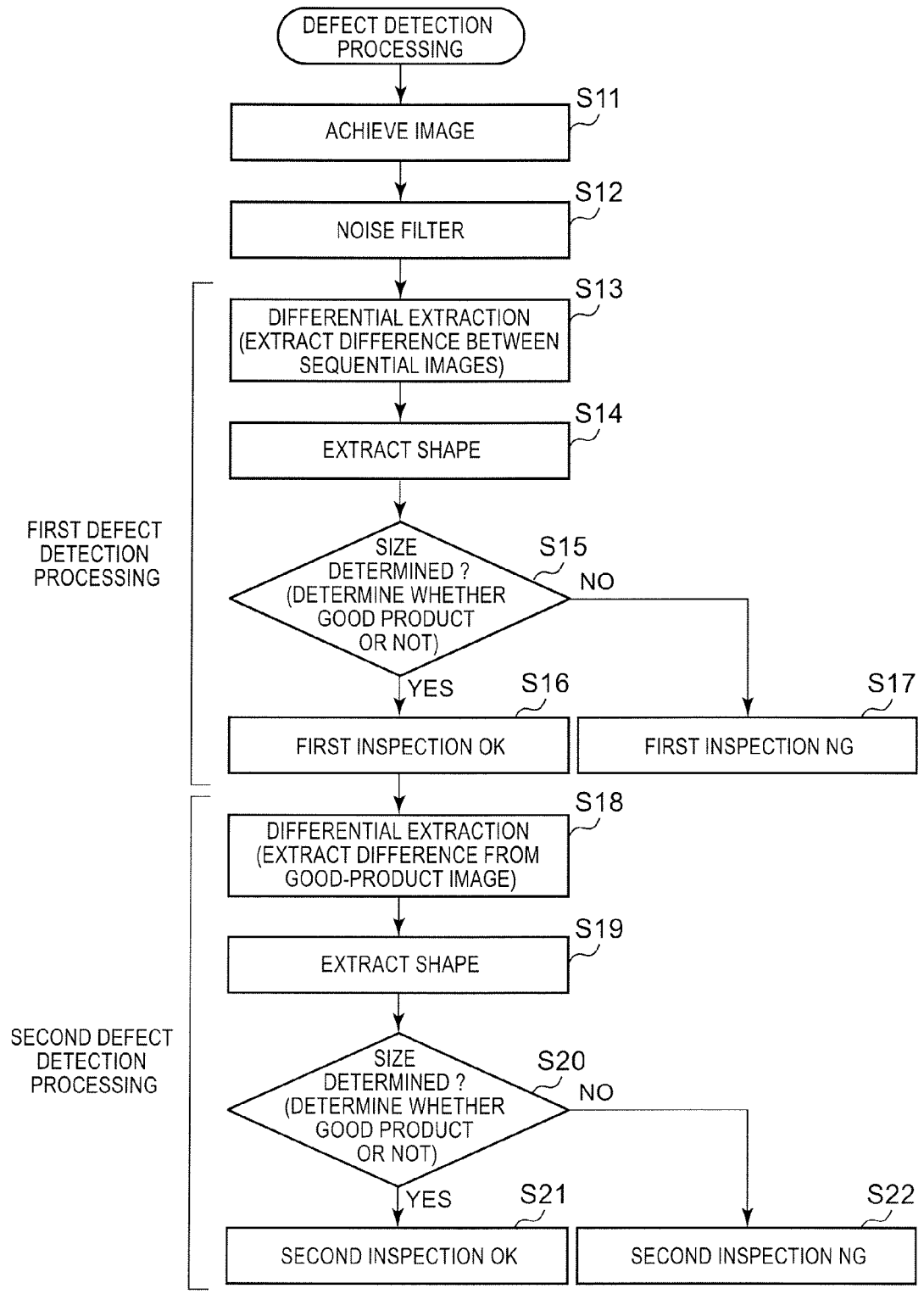
FIG. 6 is a flowchart showing defect detection processing.

FIG. 6 is a flowchart showing the defect detection processing.

First, the controller 53 achieves images picked up from the workpiece W (step S11). The pickup images are achieved under the image pickup control described above. Subsequently, the controller 53 executes noise removing processing (noise filter processing) and binary processing on the achieved pickup images data (step S12), and then executes first and second defect detection processing.

That is, the controller 53 executes differential extraction processing of achieving the difference between adjacent pickup image data which are sequentially picked up (that is, the adjacent tooth differential data) as the first defect detection processing (step S13), executes shape extraction processing for detecting an image in the differential data (pixels having connectivity) (step S14), determines the size of the detected image and determines in accordance with a determination result whether a first inspection is OK (first inspection OK) or NG (first inspection NG) (step S16, S17).

Figure 7:
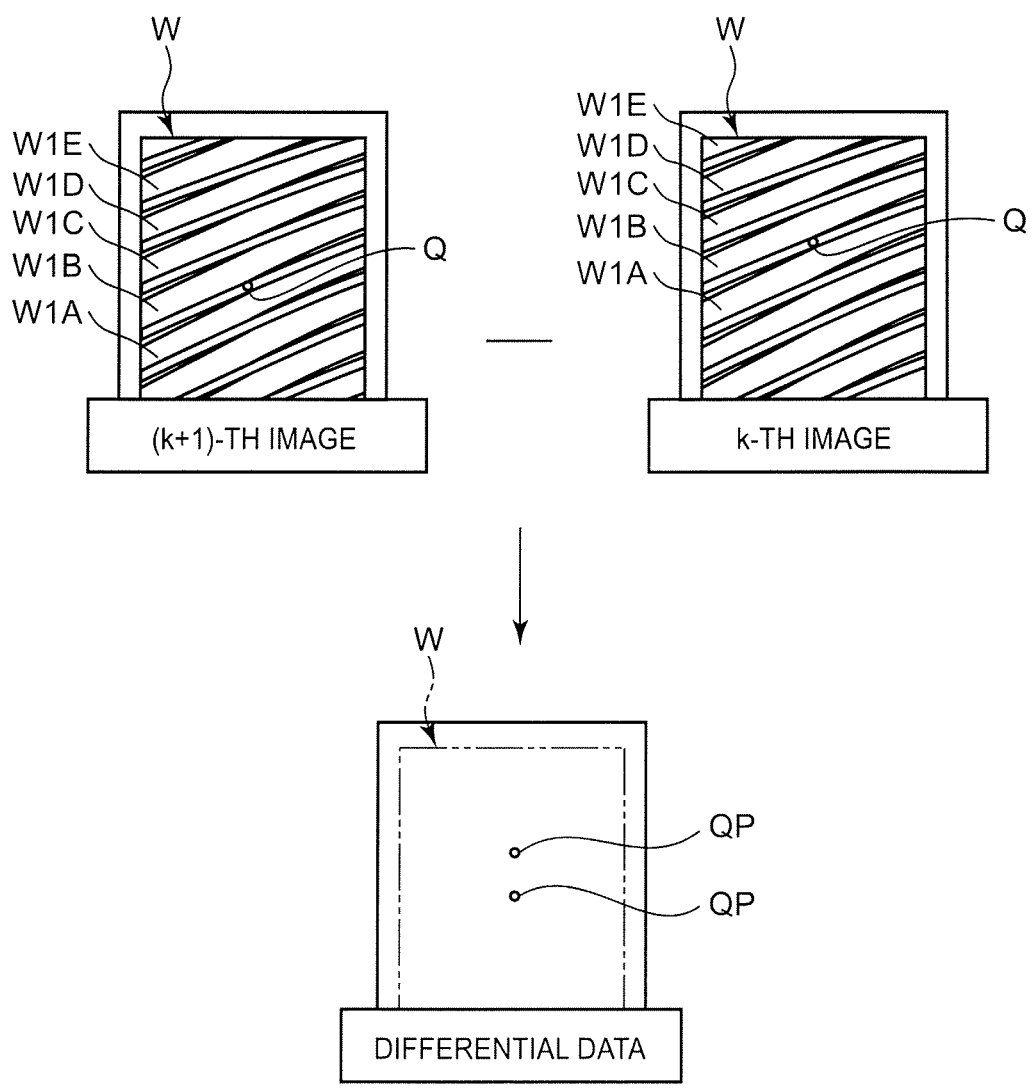
FIG. 7 is a diagram showing first defect detection.

FIG. 7 is a diagram showing the first defect detection. As shown in FIG. 7, the controller 53 achieves the difference between a pickup k-th image (k represents an integer: k=1, 2, 3, . . . ) and a pickup (k+1)-th image through image processing to obtain differential data (corresponding to step S13). In order to make the description understandable easily, the outline of the workpiece W is represented by a virtual line (two-dotted chain line) in the differential data shown in FIG. 7.

In FIG. 7, each of reference characters W1A, W1B, . . . , W1E represents a tooth portion W1 of the workpiece W, and the adjacent (sequential) pickup image data are displaced from each other tooth by tooth. In the example of FIG. 7, a surface flaw caused by a dent (represented by reference character Q) exists on the tooth surface of the tooth portion W1B.

In this case, the controller 53 detects a differential image QP corresponding to the surface flaw Q on the basis of the differential data (corresponding to step S14). In the example of FIG. 7, each of the adjacent pickup image data has the surface flaw Q, and thus two differential images QP corresponding to the surface flaw Q are detected.

Thereafter, the controller 53 determines the presence or absence of a defect by determining whether the size of the detected differential images QP is within a permissible range (corresponding to step S15).

The permissible range of the first defect detection processing (hereinafter referred to as first permissible range) is set as a determination reference value for a flaw (containing a dent). Specifically, the first permissible range is set to a value which is less than 1 mm in length. When the size of a flaw is less than 1 mm, the flaw is determined as a non-defect (first inspection OK) (step S16). On the other hand, when the size of a flaw is not less than 1 mm, the flaw is determined as a defect (first inspection NG) (step S17). In this case, when there is at least one defect, the first inspection NG is determined.

Here, with respect to a tooth surface flaw of the workpiece W, the defect shape is uneven, and the orientation (direction), angle and occurring position of a defect are unstable. Therefore, a defect appears as a bright defect represented by a bright portion or as a dark defect represented by a dark portion in a pickup image. In this embodiment, a defect is detected on the basis of the differential data between adjacent images (sequentially picked up images), and thus the defect appears in differential data regardless of whether the defect is a bright defect or a dark defect, so that the presence or absence of a tooth surface flaw can be detected with high precision.

Subsequently, when the inspection NG is determined in the first defect detection processing (step S15: NO), the workpiece W has a defect, and thus the controller 53 executes publicly known reporting processing of reporting this fact to the external, and then interrupts the defect detection processing concerned.

On the other hand, when the inspection OK is determined in the first defect detection processing (step S15: YES), the controller 53 executes the differential extraction processing of achieving the difference between pickup image data and image data of an image of a good product which is stored in a storage unit 54 in advance (i.e., an image picked up from a workpiece W as a good product under the same condition) (that is, non-defect tooth differential data) (step S18), executes the shape extraction processing of detecting an image in the differential data (pixels having connectivity) (step S19), determines the size of the detected image (step S20), and second inspection OK or second inspection NG is determined in accordance with the determination result (steps S21, S22).

Figure 8:
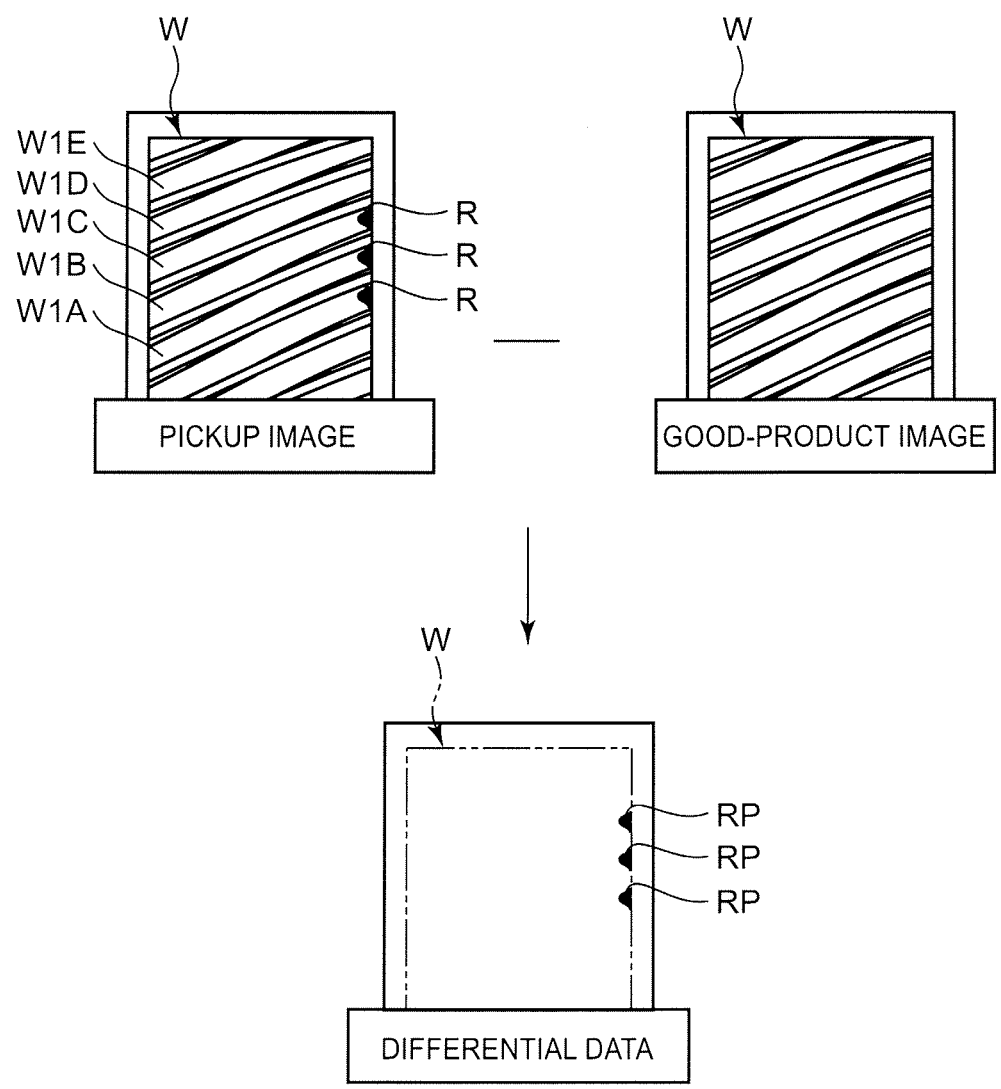
FIG. 8 is a diagram showing second defect detection.

FIG. 8 is a diagram showing second defect detection. In an example of FIG. 8, non-processed surface portions (that is, remainders of black scale represented by reference character R in FIG. 8)) remain at edge portions of the tooth portion W1C although the surface of the workpiece W is processed (cutting processing).

In this case, differential images RP corresponding to the remainders of black scale directly exist in the non-defect tooth differential data. Therefore, the controller 53 determines whether the size of each detected differential image RP is within a permissible range (corresponding to step S19).

The permissible range of the second defect detection processing (hereinafter referred to as second permissible range) is set as a determination reference value for remainders of black scale, and specifically it is set to a value less than 0.4 mm in length. Therefore, when the size of the remainder RP is less than 0.4 mm, the controller 53 determines the remainder RP as a non-defect (second inspection OK) (step S21). On the other hand, when the size of the remainder RP is not less than 0.4 mm, the controller 53 determines the remainder RP as a defect (second inspection NG) (step S22). In this case, when at least one defect exists, the second inspection NG is determined.

In the foregoing description, the size (length) of the flaw Q, etc. may be defined by the following method. However, the present invention is not limited to this method and publicly known methods may be adopted. That is, the sizes (lengths) of the flaw Q, the remainder RP, etc. may be defined by various publicly known methods. For example, these sizes (lengths) may be defined as follows. That is, there are considered all lines each of which connects any two points on the outline of the image of each flaw (remainder) on the differential image. At this time, a line having the maximum length is selected as the length of the flaw (remainder) among all the lines connecting these two points. It is needless to say that the method of defining the size (length) of the flaw (remainder) is not limited to the above method, and various publicly known methods may be adopted.

Here, the remainder of black scale of the workpiece W appears as a dark defect on a pickup image because the defect shape is planar and the surface roughness is high. Furthermore, the remainder of black scale has strong continuity, and thus it may appear as a continuous defect which is continuous over plural tooth portions W1 (tooth portions W1A to W1C in FIG. 8).

In the first defect detection processing using the differential data between the adjacent pickup images, this type of continuous defect is vanished in the differential processing and thus no defect can be detected. On the other hand, in the second defect detection processing, a defect is detected on the basis of the differential data between a pickup image of the workpiece W and a pickup image of a good product, and thus this type of continuous defect can be detected with high precision.

When a good product (workpiece) is determined through the first and second defect detection processing, the controller 53 determines the detection target workpiece W as a good product, and in the other cases, the controller 53 determines the detection target workpiece W as a defective good. Furthermore, the controller 53 executes publicly known reporting processing of reporting this fact to the external and then finishes the defect detection processing.

As described above, the workpiece inspecting apparatus according to this embodiment has the workpiece rotating mechanism 20 for outputting reference pulses PA at a fixed interval while the workpiece W is rotated at a fixed rotational speed, the image pickup mechanism 30 for picking up images of tooth portion (shape portion) W1 of the workpiece W every image pickup timing based on the reference pulses PA and the controller 53 for synchronizing the tooth portion W1 of the workpiece W and the image pickup timing on the basis of the reference pulses PA. Furthermore, the controller 53 executes the image processing of achieving the differential data between the pickup k-th (k represents an integer) image and the pickup (k+1)-th image and executes the first defect detection processing of determining on the basis of the differential data whether the workpiece W is a good product or not. Therefore, images of the workpiece W can be picked up without stopping the rotation of the workpiece W (non-stop image pickup), and thus the time required for image pickup can be shortened. In addition, as compared with a case where a defect is detected on the basis of the data of a single pickup image, the amount of data to be used for defect determination can be more greatly reduced with respect to the differential data between adjacent (sequential) pickup images, so that the time required for inspection can be shortened.

Accordingly, the total time required for the image pickup of the workpiece W and the inspection as to a good product can be shortened. Furthermore, in this embodiment, the processing load required for the inspection is small, and thus the time can be also shortened. When the processing load is small, the image pickup processing and the inspection processing can be performed in parallel in accordance with the processing capacity of the controller 53, and thus the processing time can be further shortened.

In the first defect detection processing, both of a bright defect and a dark defect in a pickup image can be detected as a defect, and thus there is achieved such an effect that a general defect such as a tooth surface flaw or the like (a defect excluding a continuous defect) can be detected with high precision.

In this embodiment, the second defect detection processing as another inspecting procession for detecting a defect on the basis of the differential data between a pickup image and an image of a good product which is stored in advance is executed, and thus a continuous defect such as a remainder of black scale or the like can be also detected with high precision. In addition, when no defect is detected in each of the first defect detection processing and the second defect detection processing, the workpiece W being inspected is determined as a good product, and thus the determination of a good product can be performed with high precision.

Furthermore, the image pickup mechanism 30 is equipped with the pulse output mechanism 40 having the workpiece detecting jig (rotator) 41 which rotates integrally with the workpiece W and has the pseudo tooth portion 41A as the detection target portion at the same angular interval as the tooth portion W1 of the workpiece W with respect to the rotation center, and the proximity sensor 42 for outputting a workpiece pulse PW every time the pseudo tooth portion 41A of the workpiece detecting jig 41 is detected, and the pulse counter 52 for counting the interval between workpiece pulses PW on the basis of the reference pulses PA to achieve a pulse number corresponding to the interval. Furthermore, the image pickup mechanism 30 picks up images of the workpiece W at the image pickup timing based on the reference pulses PA by using the workpiece pulse PW as a trigger, and picks up images of the workpiece W at the image pickup timing based on the reference pulses PA every time the reference pulses PA whose number corresponds to the pulse number are output from the image pickup timing.

According to this construction, the image pickup can be performed on the basis of the reference pulses PA at the motor 22 side while matched with the tooth portion W1 of the actual workpiece W. Therefore, the images of the respective tooth portions W1 can be picked up under the same condition (at the same position) with high precision while performing the non-stop image pickup. The enhancement of the image pickup precision also enhances the detection precision of the first defect detection processing and the second defect detection processing, and also the workpiece W can be rotated at high speed with keeping this detection precision, so that the detection timing can be further shortened.

That is, according to this construction, the images of the tooth portions W1 which are periodically and repetitively formed on the workpiece W can be picked up with high precision, and the defect detection based on the difference between pickup images and also the defect detection based on the difference between a pickup image and an image of a good product are performed, whereby both of the enhancement of the defect detection precision and the shortening of the total time required for the image pickup and the inspection can be performed.

<Blowing Device>

Subsequently, a blowing device (inclusion removing device) 80 for blowing the workpiece W will be described.

Figure 9:
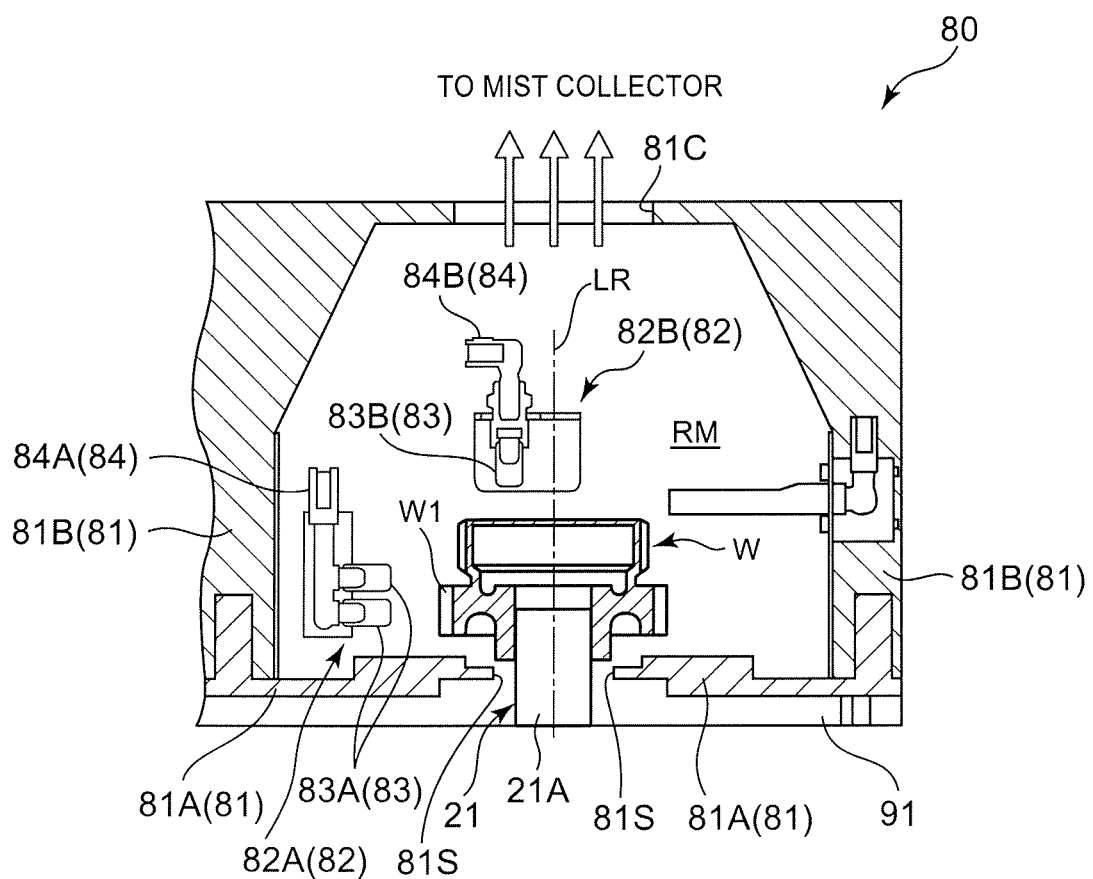
FIG. 9 is a diagram showing a blow device.

FIG. 9 is a diagram showing the blowing device 80. This blowing device 80 is used between the cleaning step and the inspecting step shown in FIG. 1, and it comprises a gas jetting device for jetting (blowing) gas (air in this embodiment) to the workpiece W to drop cleaning liquid or the like remaining on the workpiece W which has been passed through the cleaning step. The workpiece W is shifted to the inspecting step containing the image pickup processing based on the workpiece inspecting apparatus 10 with keeping the setting of the blow device 80. In FIG. 9, the same portions as shown in FIG. 9 are represented by the same reference numerals, that is, the holder portion 21 (containing the shaft portion 21A) for fixedly holding the workpiece W also serves as the holder portion 21 used for the inspection performed by the workpiece inspecting apparatus 10, and it is freely rotatable. In FIG. 9, reference character LR represents a rotational axial line of the workpiece W.

As shown in FIG. 9, the blowing device 80 has an enclosing portion 81 for enclosing the surrounding area of the workpiece W held on the holder portion 21, and a blow portion 82 disposed in the surrounding portion 81. A withdrawing storage 91 for withdrawing mist (inclusion containing solid material and oil) containing cleaning liquid and workpiece attached material (oil, dust, metal (cut powder)) is disposed below the workpiece W, and a mist collector (not shown) is disposed above the workpiece W.

The surrounding portion 81 has a bottom plate 81A which surrounds the lower portion of the workpiece W, and a surrounding wall 81B which surrounds the side of the workpiece W over the periphery thereof. A processing chamber RM which is gradually narrowed upwardly is formed by the surrounding wall 81B, and an opening portion 81C which is opened to the mist collector (not shown) is formed at the upper side of the workpiece W. The mist collector functions as a mist discharging blower for sucking mist in the processing chamber RM and discharging the sucked mist to the outside.

The blow portion 82 is disposed around the workpiece W in the processing chamber RM, and the surrounding of the workpiece W is shielded by the surrounding portion 81. In this construction, the blow portion 82 has a tooth surface targeting blow portion (side blow portion) 82A for blowing the tooth surfaces (the surfaces of the tooth portions W1), and an end face targeting blow portion (upper blow portion) 82B for blowing the end faces of the tooth surfaces (tooth portions W1).

Each of the blow portions 82A and 82B has nozzles 83 facing the tooth surface and the end face respectively, and discharges air supplied through each air supply pipe 84 (84A, 84B) from each nozzle 83 to the workpiece W.

More specifically, the tooth surface targeting blow portion 82A is designed to be wide-ranging so as to extend in the width direction of the tooth surface (in the up-and-down direction in FIG. 9), and has plural nozzles 83A (two nozzles 83A in this embodiment) arranged so as to be spaced from one another in the width direction of the tooth surface. Accordingly, air is jetted (blown) to the overall area in the width direction of the tooth surfaces. By jetting (blowing) air from each nozzle 83A to the rotating workpiece W, the overall tooth surfaces can be subjected to air blowing.

The end face targeting blow portion 82B has a wide-ranging nozzle 83B extending in a direction which is substantially along the end face of the workpiece W (in the vertical direction (the direction of gravitational force) in FIG. 9). Air from the nozzle 83B is jetted to the rotating workpiece W, whereby the overall end face of the workpiece W can be blown with air.

In the blow step (mist step), mist, etc. containing cleaning liquid and workpiece inclusion (oil, dust, metal (cut powder)) are passed through a gap 81S formed between the holder portion 21 and the bottom plate 81A and then withdrawn into the withdrawing storage (withdrawing step). Air which is jetted (blown) after the cleaning step is passed through this gap 81S and the open portion 81C at the upper side and then discharged to the outside.

According to this embodiment, as shown in FIG. 9, the tooth surface targeting blow portion 82A is disposed at the side of the workpiece W so that the nozzles 84A are horizontally oriented, and the end face targeting blow portion 82B is disposed above the workpiece W so that the nozzle 83B is oriented downwardly. Therefore, air can be orthogonally jetted (blown) to the workpiece W from the side and upper side. According to this air blowing structure, materials (inclusions) attached to each workpiece W can be removed in a short time as compared with a case where any one of the blow portions 82A and 82B is used.

That is, the materials (oil, dust, metal (cut powder), cleaning liquid) attached to the tooth surfaces can be removed relatively excellently by only the tooth surface targeting blow portion 82A. However, in this case, the removing force of removing these materials from the end face of the workpiece W is lowered and thus there occurs such a risk that remainders on the end face are detected as defects. Furthermore, the materials (oil, dust, metal (cut powder), cleaning liquid) attached to the end face of the workpiece W can be removed relatively excellently by only the end face targeting blow portion 82B. However, in this case, the removing force of removing the materials from the tooth surfaces of the workpiece W is lowered, and thus the material easily remain between the tooth portions W1.

On the other hand, according to this embodiment, both the tooth surface targeting blow portion (side blow portion) 82A and the end face targeting blow portion (upper blow portion) 82B are used, and air is jetted (blown) to the workpiece W from both the sides (from the side and the upper side of the workpiece W) at the same time, whereby the capacity of removing remainders from the overall workpiece W can be enhanced and the removal can be performed in a short time. According to the inventors' experiment, in this embodiment, the residual amount of remainders can be set to a target amount (2% or less) (a removal requirement is 98% or more) in a blow time of 4 seconds or more.

In addition, the workpiece inspecting apparatus is equipped with the mist collector for sucking from the upper side of the processing chamber RM mist which occurs due to air jetting from both the blow portions 82A, 82B, and the mist collector is driven to discharge the mist when the blowing operation is carried out, so that re-attachment of the mist to the workpiece W can be prevented. The construction of the blowing device 80 is not limited to the above construction, and other publicly known blowing devices may be used.

Second Embodiment

According to a second embodiment, an illumination device 100 is added to the workpiece inspecting apparatus 10 according to the first embodiment.

In order to enhance the inspection precision when a workpiece W is inspected on the basis of pickup images as described above, it is important to pickup clear images of a defect portion of the workpiece W. In addition, according to this workpiece inspecting apparatus 10, the images of the workpiece W are picked up while rotating the workpiece W. Therefore, it is desired to increase the shutter speed by illuminating the workpiece W (shortening the exposure time) and thus pick up images of the workpiece W with no blur.

In this case, it is considered to dispose an illuminating device for illuminating a workpiece W when images of the workpiece W are picked up (image pickup step).

However, the workpiece W of this embodiment is a metal gear wheel which has a substantially circular shape in plan view and on which tooth portions W1 are periodically repeated along the peripheral direction of the workpiece W, and thus it has such a shape that a convex (projecting) shape, a concave (recessed) shape and an R shape are repeated. Therefore, reflection of illumination light from the workpiece W is diversified (for example, illumination light is reflected in various directions). In addition, the surface of the gearwheel is ground (so-called tooth ground gear), and thus the surface thereof serves as a mirror surface and easily reflects illumination light, which generates shadow caused by toot portions, that is, tooth shadow. Accordingly, there occurs a situation that unevenness of brightness occurs and this unevenness of bright is erroneously detected as a defect portion.

Furthermore, defects of a workpiece W occur at various positions such as a tooth tip, a tooth base, a tooth end, etc., and the types of defects are various like a dent, a chip, a black scale, a flaw, etc. Therefore, there occurs a situation that the brightness (contrast) varies every defect. For example, "dent" has a uniformly recessed shape, and it is liable to become a darker dark portion (dark defect) than the surrounding thereof. Furthermore, "chip" has plural kinds of cut faces, and thus at least a part thereof becomes a reflection surface, so that it is liable to become a brighter bright portion (bright defect) than the surrounding thereof. Furthermore, "black scale" becomes a dark portion (dark defect) and "flaw" is liable to become a bright portion (bright defect).

This means that both the bright portion and the dark portion may be defects and thus it is necessary to secure sufficient contrast (defect contrast) in order to detect these defects.

Therefore, according to this embodiment, in order to countermeasure the unevenness of brightness (countermeasure to tooth shadow) and secure defect contrast, the workpiece inspecting apparatus adopts an image pickup layout using a large-size illuminating device based on pseudo coaxial illumination.

Figure 10:
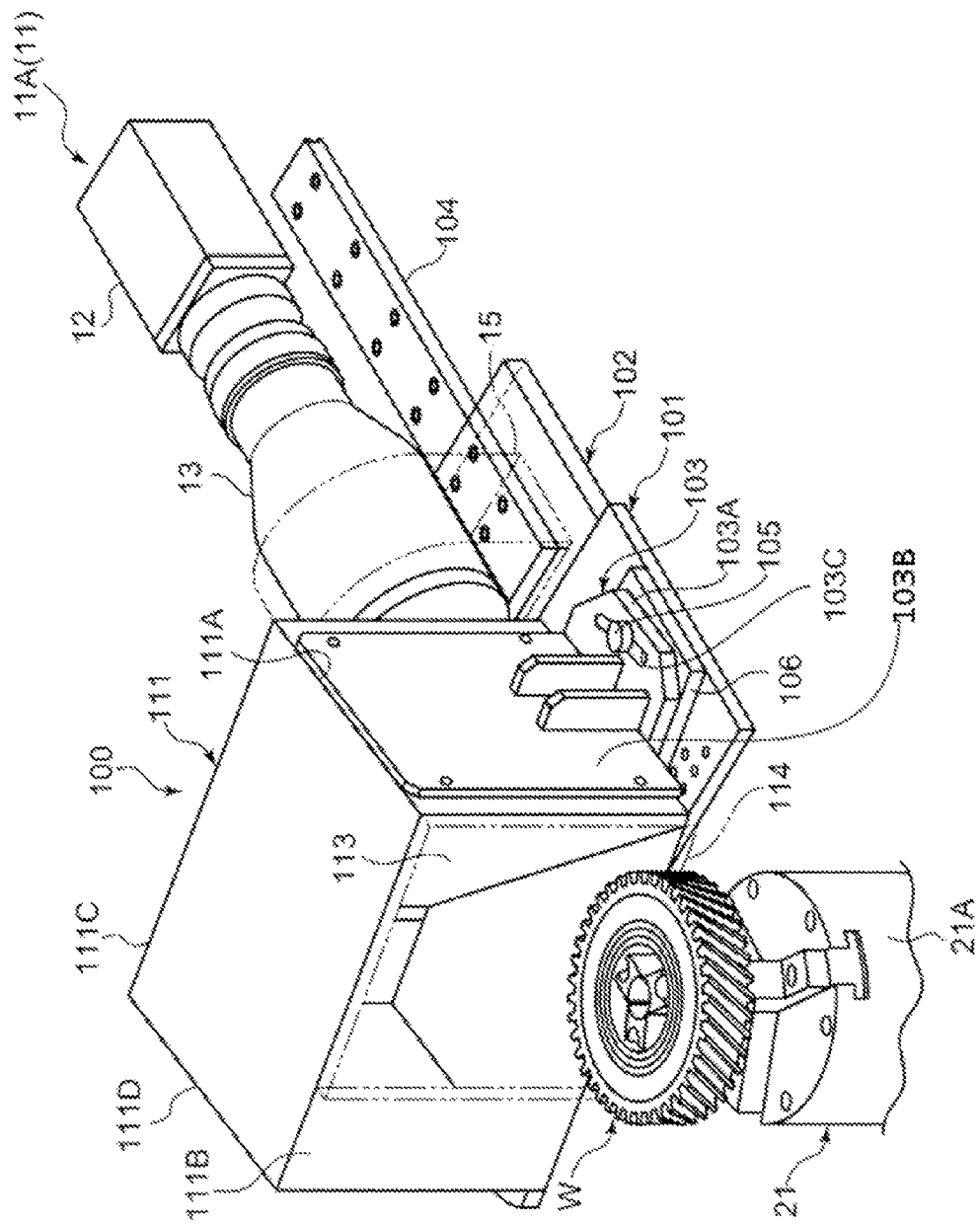
FIG. 10 is a perspective view showing an image pickup (imaging) layout.
Figure 11:
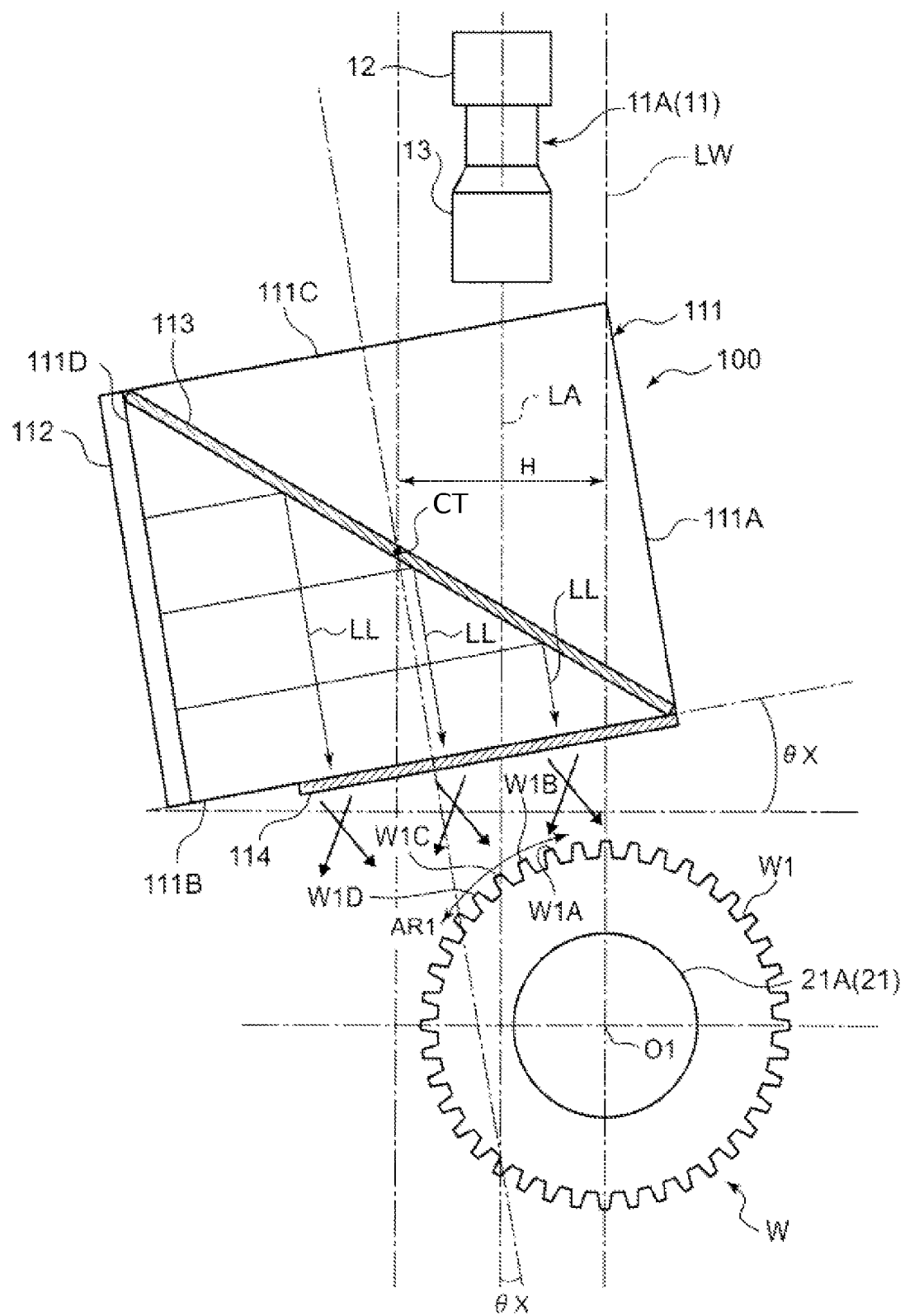
FIG. 11 is a top view of the image pickup layout.

FIG. 10 is a perspective view showing the image pickup layout of this embodiment, and FIG. 11 is a top view showing the image pickup layout. In these figures, the image pickup layout of a tooth surface image pickup camera 11A (hereinafter referred to as camera 11A) is shown.

As shown in FIGS. 10 and 11, a horizontal plate type pedestal (a pedestal for the illuminating device) 101 and a horizontal plate type pedestal (a pedestal for a camera) 102 are disposed in the neighborhood of the workpiece W fixed to the holder portion 21 so that the horizontal plate type pedestal 102 is farther away from the workpiece W than the pedestal 101. The illuminating device 100 is secured through a securing jig 103 to the pedestal 101 nearer to the workpiece W, and the camera 11A is supported on the pedestal 102 farther away from the workpiece W so as to be freely movable linearly through a rail 104 between the workpiece W side and the opposite side. These two pedestals 101 and 102 may be unified as a single pedestal or may be provided separate pedestals.

As shown in FIG. 10, the camera 11A has a camera body 12, and a lens 13 connected to the camera body 12. The lens 13 is mounted on the pedestal 102 so that the lens optical axis LA (see FIG. 11) coincident with the center of an image pickup area is coincident with the moving direction along the rail 104. Therefore, the distance between the camera 11A and the workpiece W (the separation distance) can be adjusted. For example, when the workpiece W is large (a gear wheel has a large diameter), the camera 11A is moved to be farther away from the workpiece 11A, and when the workpiece W is small (the gear wheel has a small diameter), the camera 11A is made to approach to the workpiece W, whereby the camera position can be easily adjusted.

Specifically, as shown in FIG. 11, the lens optical axis LA is offset (displaced) from a workpiece center passing axis LW (in FIG. 11) which passes through the rotational center O1 of the workpiece W and extends in the radial direction of the workpiece W so as to be spaced from the workpiece center passing axis LW in parallel by only a distance H. The camera 11A is movable along the lens optical axis LA, and the position of the camera 11A is fixed by a fixing member (not shown).

The camera 11A is set by the offset amount (the distance H), selection of the lens 13 (containing selection of magnification) and the adjustment of the distance between the workpiece W and the camera 11A so that an image simultaneously containing four or more tooth portions (W1A to W1D) in the same visual field can be picked up as shown in FIGS. 7 and 8.

Reference numeral 15 in FIG. 10 represents a lens holding member for holding the lens 13, and reference character AR1 in FIG. 11 represents an image pickup area of the camera 11A. The number of toot portions which are simultaneously contained in the image pickup area may be two or more (that is, plural tooth portions may be simultaneously contained in the image pickup area).

As shown in 10, the securing jig 103 is integrally equipped with a horizontal plate portion 103A mounted on the pedestal 101, and a wall portion 103B erected vertically from the horizontal plate portion 103A. The illuminating device 100 is mounted on the horizontal plate portion 103A, and the wall portion 103B and the illuminating device 100 are fixed to each other by a fixing member (for example, a fastening bolt) 105 under the state that the side surface 111A of the illuminating device 100 is brought into contact with the wall portion 103B. A plate member 106 is interposed between the securing jig 103 and the pedestal 101, and by adjusting the thickness of the plate member 106, the height of the illuminating device 100 is adjusted so that clear images of the workpiece W can be picked up.

An elongated groove 103C which penetrates in the vertical direction and extends arcuately in the horizontal direction is formed in the horizontal plate portion 103A of the securing jig 103, and a fixing member (for example, a fastening bolt) is inserted in the elongated groove 103C and fixed to the pedestal 101, whereby the securing jig 103 is fixed to the pedestal 101. According to this fixing structure, the fixing position of the securing jig 103 can be changed within the length range of the elongated groove 103C, whereby the position and orientation of the illuminating device 100 with respect to the workpiece W can be easily adjusted.

The illuminating device 100 emits uniform illumination light substantially coaxially to an illumination target (workpiece W), and it has a hollow housing 111 of a rectangular parallelepiped in which a light source 112, a half mirror 113 and a diffuser panel 114 are provided as shown in FIGS. 10 and 11. FIG. 10 shows the internal construction of the illuminating device 100.

The housing 111 has a front face 111B which is opened and located at the workpiece W side, and also a back face 111C which is opened and located at the camera 11A side to face the front face 111B. The camera 11A is located so that images of the workpiece W can be picked up through these openings and the half mirror 113. The light source 112 is a surface-emitting light source which is provided on the side surface 111D of the housing 111 and emits uniform light to the half mirror 113 over a broad range. Emission light (represented by arrows in FIG. 11) is reflected from the half mirror 113, and then emitted from the front face 111B of the housing 111 to the image pickup area AR1 of the workpiece W.

That is, the housing 111 functions as an optical path portion through which light emitted to the image pickup area AR1 of the workpiece W passes, and substantially uniform illumination light is irradiated so that the optical axes LL of light beams passing through the optical path portion are parallel to one another.

The diffuser panel 114 comprises a transmission type diffusion panel, and it is disposed so as to cover the front face 111B as an emission port of the housing 111, converts the illumination light from the housing 111 to diffusion light and then emits the diffusion light to the workpiece W.

As shown in FIG. 11, according to this embodiment, the optical axis (the optical axis of the optical path portion) LL of the housing 111 is set to be oblique with respect to the tooth portion W1 in the image pickup area AR1 of the workpiece W. More specifically, according to this embodiment, the tooth portion W1 as an inspection target in the image pickup area AR1 corresponds to four tooth portions represented by W1A to W1D, and the tooth portions W1A to W1D as the inspection target are set as the reference tooth portions W1. The optical axis LL of the housing 111 (the optical axis of the optical path portion) is inclined with respect to the optical axis LA of the lens 13 by only an angle θX in plan view (corresponding to the side view of the workpiece W) so that illumination light reaches the overall surface of the reference tooth portions W1 (W1A to W1D) when viewed from the camera 11A side.

Figure 12:
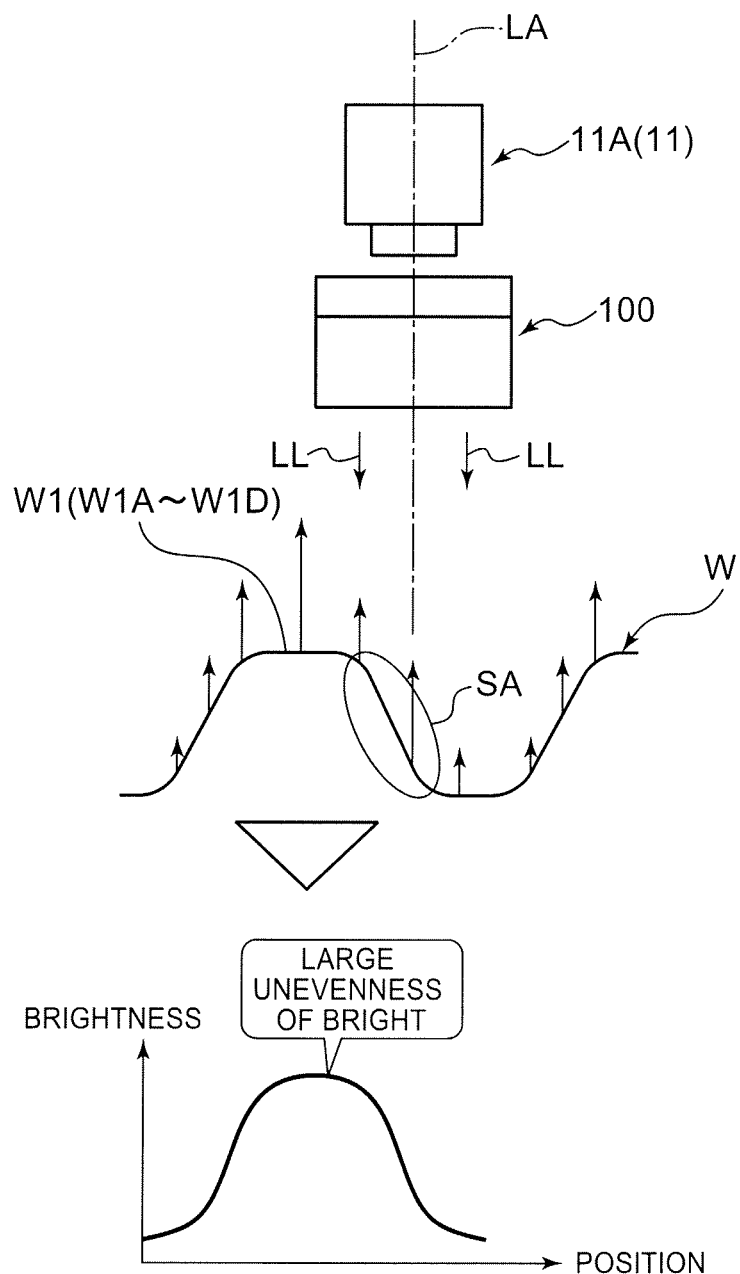
FIG. 12 is a diagram showing a case where an optical axis of illumination light is not inclined with respect to a lens optical axis.

FIG. 12 is a diagram showing a case where the optical axis LL of the illumination light is not inclined with respect to the lens optical axis LA, and FIG. 13 is a diagram showing a case where the optical axis LL is inclined with respect to the lens optical axis LA by only the angle θX. FIGS. 12 and 13 schematically show a case where an image of a tooth face in an area represented by SA is picked up by the camera 11A.

As shown in FIG. 12, when the optical axis LL of illumination light is not inclined, with respect to the toot portion W1 (any one of W1A to W1D) as an inspection target, the amount of reflection light traveling to the camera 11A is larger at the tooth tip, and smaller at the tooth base, etc. Therefore, the brightness is highest at the tooth tip and lowest at the tooth base, and thus brightness unevenness between the tooth tip and the tooth base is larger, that is, the brightness unevenness of the tooth face represented by SA is large. This brightness unevenness lowers the defect detection precision of the tooth face.

On the other hand, as shown in FIG. 13, when the optical axis LL of the illumination light is inclined by only the angle θX, the illumination light reaches the overall surface (the tooth tip, the tooth base and the tooth end) when viewed from the camera 11A side, and the illumination light is obliquely applied to the tooth tip. Therefore, the amount of reflection light which is reflected from the tooth tip to the camera 11A is smaller as compared with the case of FIG. 12, and the brightness unevenness between the tooth tip and the tooth base can be reduced. Accordingly, in FIG. 13, the brightness unevenness of the tooth face represented by SA can be reduced.

In other words, according to this embodiment, the optical axis LL of the illumination light is inclined obliquely so that the brightness unevenness of the tooth portions W1A to W1D as an inspection target is reduced. According to this embodiment, the angle θX is set to a value in the range from 5° to 20°. Accordingly, the brightness unevenness of the tooth face, etc. in the pickup image can be reduced, the defect contrast of the tooth face can be secured and the defect detection precision can be enhanced.

In addition, as shown in FIG. 11, the illumination light is converted to the diffusion light by the diffuser panel 114 and applied to the workpiece W. Therefore, the influence of the shape of the tooth portions W1 of the workpiece W can be reduced and the brightness unevenness in the pickup image can be more greatly reduced, whereby the defect detection precision can be also enhanced.

Furthermore, according to this construction, as shown in FIG. 11, the lens optical axis LA of the camera 11A is offset (displaced) from the workpiece center passing axis LW in parallel in plan view, the illumination center CT of the illuminating device 100 is disposed at the opposite side to the workpiece center passing axis LW with respect to the lens optical axis LA in plan view (the side view of the workpiece W), and the illuminating device 100 is tilted with the illumination center CT set at the center so that the light emission side (the front face 111B) of the illuminating device 100 faces the rotational center O1 side of the workpiece W.

According to this layout, one side (the left side in FIG. 11) with respect to the workpiece center passing axis LW is subjected to image pickup by the camera 11A, the illumination light can be applied to the image pickup area AR1, and occurrence of tooth shadow is suppressed while picking up images of plural tooth portions W1.

In a case where the lens optical axis LA of the camera 11A is set to be coaxial with the workpiece center passing axis LW, with respect to the respective tooth portions W1 of the workpiece W, the tooth tips project to one side (left side) at one side (for example, the left side) of the workpiece center passing axis LW while the tooth tips project to the other side (right side) at the other side (for example, the right side) of the workpiece center passing axis LW, so that tooth shadow is liable to occur at any one side of the workpiece center passing axis LW. However, according to the above layout, the situation that the tooth shadow occurs can be avoided, whereby the brightness unevenness in the pickup image can be suppressed and the defect detection precision can be enhanced.

Furthermore, according to this construction, the tooth portions W1A to W1D at the four places are contained in the pickup image, and the illumination environment for the tooth portions W1A to W1D (the direction of the illumination light, etc.) by the illuminating device 100 is slightly different among these tooth portions. Therefore, the image pickup is performed under the illumination environment which varies every inspection target tooth portion (W1A to W1D), and the defect detection processing (first defect detection processing) based on the adjacent tooth difference, etc. are performed under the different illumination environments. Therefore, a defect which cannot be detected under some illumination environment can be detected under a different illumination environment. Accordingly, any defect can be suppressed from being overlooked.

That is, in this embodiment, four inspecting timings are provided for one tooth portion. Furthermore, with respect to the tooth portions W1A, W1B, W1C and W1D whose images are picked up by the camera 11A, the average brightness of each of the tooth portions W1A to W1D to be captured varies successively. In other words, the luminosity (brightness) varies, and thus the illumination environment varies. Furthermore, for example with respect to the brightness of the surface of the tooth portion W1A, it varies gradually continuously gently with no brightness unevenness as shown in FIG. 13. The same is applied to the other tooth portions (W1B to W1D).

In order to vary the brightness of the surface of the tooth portion whose image is picked up, the direction of the illumination light may be varied. In this case, it is necessary to provide plural illumination light sources, and thus this method is not useful from the viewpoint of the space of the apparatus and the cost. Therefore, according to this embodiment, only one light source is used. Furthermore, in order to capture the variation of the brightness of the surface of the tooth portion under one light source, plural image pickup cameras are necessary. However, this method is not useful from the viewpoint of the space of the apparatus and the cost. Therefore, according to this embodiment, the number of tooth portions which can be simultaneously contained in the image pickup area of a single image is set to plural number (two or more), and plural inspecting timings are set for each tooth portion.

In this construction, under an illumination environment which varies gradually continuously gently without brightness unevenness and under which the luminosity (brightness) of each of the tooth portions W1A to W1D successively varies, plural pickup images are obtained for one tooth portion under plural illumination environments under which the luminosity is different. Therefore, plural pickup images can be obtained for each tooth portion under plural illumination environments having different luminosities, and each pickup image is inspected, whereby plural inspecting timings can be set for each tooth portion. Accordingly, any defect can be suppressed from being overlooked.

Here, FIGS. 14A, 14B and 14C show comparison examples of the illuminating device 100. FIG. 14A shows a case where a thin diffused illumination type illuminating device 100A is used. The illuminating device 100A has a light transmissible type thin illuminating device 131 and as transmission type diffuser panel 114. The thin illuminating device 131 is disposed between the camera 11A and the workpiece W so as to apply illumination light in the coaxial direction with the lens optical axis LA of the camera 11A.

This thin illuminating device 131 may be constructed by a publicly known thin illuminating device having a light source 131A and a transmission type light guiding unit 131B for applying light from the light source 131A through a light guiding plate or the like to the outside. According to this illuminating device 100A, the thin illuminating device is used, and thus there is an advantage that light can be illuminated to a broad area, the space can be saved and the position and orientation of the illuminating device can be easily adjusted. However, according to inventors' studies, it is difficult to secure a light amount sufficient to image pickup.

FIG. 14B shows a case where a planar diffusion composite illumination type illuminating device 100B is used. In this illuminating device 100B, two publicly known planar illuminating devices 133 and 134 are used as light sources. One illuminating device 133 is disposed so as to face the tooth faces of the image pickup area AR1, and the other planar illuminating device 134 is disposed at the sides of the tooth portions W1A to W1D of the image pickup area AR1. Transmission type diffuser panels are disposed at the emission faces of the planar illuminating devices 133, 134 so that diffusion light is emitted from each of the planar illuminating devices 133, 134.

According to this illuminating device 100B, light is illuminated in two directions (from two sides), and thus there is an advantage that brightness can be secured in abroad range. However, there is a disadvantage that strong brightness unevenness appears due to tooth shadow, it is difficult to adjust the position and orientation of the illuminating devices, and also it is difficult to dispose the illuminating devices with avoiding interference with other cameras (the camera 11B for the tooth tips of the workpiece, the camera 11C for the end face of the workpiece, etc.).

FIG. 14C shows a case where a dome illumination type illuminating device 100C is used.

In this illuminating device 100C, a publicly known dome illuminating device 136 is used as a light source. The dome illuminating device 136 has plural light sources 136A, and a bowl type housing 136B for reflecting light from the light source 136A in various directions, and it is disposed between the camera 11A and the workpiece W.

According to this illuminating device 100C, there are advantages that diffusion light can be emitted to the workpiece W over a broad range, the brightness unevenness can be suppressed and the position and orientation of the illuminating device 100C can be easily adjusted. However, according to the inventors' studies, it is difficult to secure a light amount sufficient to image pickup.

From these comparison result, it is determined that the illuminating device 100 of this application is optimum because there are advantages that the light amount sufficient to image pickup can be secured, the brightness unevenness can be suppressed, the position and orientation of the illuminating device can be adjusted and the illuminating device can be easily disposed with avoiding the interference with the other cameras.

As described above, the inspecting apparatus of this embodiment has the workpiece rotating mechanism 20 for outputting the reference pulses PA at a fixed interval while rotating the workpiece W at a fixed rotational speed, the image pickup mechanism 30 for picking up images of the workpiece W every fixed period based on the reference pulses PA so that two or more tooth portions (shape portions) W1 of the workpiece W are contained in each pickup image, the controller 53 for synchronizing the tooth portion W1 of the workpiece W with the image pickup timing on the basis of the reference pulses PA, and the illuminating device 100 for obliquely illuminating light to the tooth portions W1 (W1A to W1D) as a reference within the image pickup area AR1 when the image pickup is performed by the image pickup mechanism 30. The controller 53 executes the first defect detection processing of executing the image processing of obtaining the difference between the k-th pickup image (k represents an integer) and a (k+1)-th pickup image and detecting a defect on the basis of the differential data. Therefore, the images of the workpiece W can be picked up without stopping the workpiece W (non-stop image pickup) while the brightness unevenness is suppressed by the illuminating device 100, and thus the time required for the image pickup can be shortened. In addition, as compared with the case where a defect is detected on the basis of data of a single pickup image, the amount of target data used to determine a defect can be reduced when the differential data between the adjacent images are used, and thus the time required to inspect the workpiece W can be shortened. Accordingly, defects can be prevented from being overlooked due to brightness unevenness while shortening the total time required for the image pickup and inspection of the workpiece W.

Furthermore, according to this construction, images can be picked up under different illumination environments for each tooth portion W1 during image pickup, whereby the defect detection precision can be also enhanced and overlooking of defects can be suppressed more greatly.

Still furthermore, according to this construction, the processing load required for the inspection of the workpiece W is small, and thus the inspecting time can be also shortened. When the processing load is small, both the image pickup processing and the inspection processing can be simultaneously performed in parallel in accordance with the processing capacity of the controller 53, and thus the time can be also shortened.

Still furthermore, in the first defect detection processing, both the bright defect and the dark defect in the pickup image can be detected as defects, and thus there is an effect that general defects such as a tooth face flaw, etc. (defects excluding a continuous defect) can be detected with high precision.

In this construction, the workpiece W is a gear wheel having a substantially circular section in plan view on which tooth portions (shape portion) W1 are periodically repeated along the peripheral direction of the workpiece W, and the illuminating device 100 obliquely applies light to the tooth portions W1 as references in the image pickup area AR1. Therefore, the brightness evenness can be reduced at the tooth tips and the tooth bases while light is applied to the overall surfaces of the tooth portions (the tooth tips, tooth bases and the tooth ends) when viewed from the image pickup mechanism 30 side, and the overlooking of defects can be reduced.

In addition, the illuminating device 100 has the transmission type diffuser panel 114 for converting light to diffusion light and applying the diffusion light to the image pickup area AR1, so that the brightness unevenness in the pickup image can be more greatly reduced and the overlooking of defects can be more greatly suppressed.

Furthermore, the illuminating device 100 has the housing 111 functioning as the optical path portion through which light travels to the image pickup area AR1 of the image pickup mechanism 30, the optical axis LL of the optical path portion is oblique to the tooth portion W1 as a reference within the image pickup area AR1, and the diffuser panel 114 is provided at the emission side of the optical path portion. Therefore, there is an effect that by adjusting the position and orientation of the housing 111, the illuminating device 100 can be easily adjusted so that the unevenness of brightness of the tooth portion W1 as the reference is suppressed, and installation performance is excellent. Specifically, when the fixing member 105 (see FIG. 9) is loosened, the position and orientation of the housing 111 can be easily adjusted.

In this case, the optical axis LL of the illumination light is set to be oblique to the lens optical axis LA of the image pickup mechanism 30, whereby the unevenness of brightness in the pickup image can be efficiently reduced.

In this construction, as shown in FIG. 11, the lens optical axis LA of the image pickup mechanism 30 is offset (displaced) in parallel from the workpiece center passing axis LW which passes through the rotational center O1 of the workpiece W and extends in the radial direction of the workpiece W in plan view, the illumination center CT of the illuminating device 100 is disposed at the opposite side to the workpiece center passing axis LW with respect to the lens optical axis LA in plan view, and the emission side of the illuminating device 100 is tilted to the rotational center O1 side of the workpiece W with respect to the illumination center CT. Therefore, tooth shadow can be prevented from occurring while picking up images of plural tooth portions W1.

Furthermore, according to this construction, the second defect detection processing as the other inspecting processing for detecting a defect on the basis of the differential data between a pickup image and a pre-stored image of a good product is executed, and thus a continuous defect such as a remainder of black scale or the like can be detected with high precision. In addition, when no defect is detected by each of the first defect detection processing and the second defect detection processing, the workpiece is determined as a good product. Accordingly, a good product can be determined with high precision.

In addition, according to this construction, the image pickup mechanism 30 is equipped with the pulse output mechanism 40 having the workpiece detecting jig (rotator) 41 having the pseudo tooth portions 41A serving as the detection target portions which are rotated integrally with the workpiece W and arranged at the same angular intervals as the tooth portions W1 of the workpiece W with respect to the rotational center, the proximity sensor 42 for outputting a workpiece pulse PW every time the pseudo tooth portion 41A of the workpiece detecting jig 41 is detected, and the pulse counter 52 for counting the interval between the workpiece pulses PW on the basis of the reference pulses PA and achieving the pulse number corresponding to the interval. The image pickup mechanism 30 picks up images of the workpiece W at the image pickup timing based on the reference pulses PA by using the workpiece pulse PW as a trigger, and picks up the images at the image pickup timing based on the basis of the reference pulses PA every time the reference pulses PA whose number corresponds to the pulse number concerned are output from the image pickup timing.

According to this construction, the image pickup can be performed on the basis of the reference pulses PA at the motor 22 side while matched with the tooth portions W1 of the actual workpiece W. Therefore, the images of the respective tooth portions W1 can be picked up under the same condition (at the same position) with high precision with performing the non-stop image pickup. The enhancement of the image pickup precision enhances the detection precision for the first defect detection processing and the second defect detection processing, and the workpiece W can be rotated at a high speed with keeping this detection precision, whereby the inspecting time can be more remarkably shortened.

That is, according to this embodiment, the defect detection based on the difference between the pickup images (sequential or adjacent images) and the detect detection based on the difference between the pickup image and the good-product image are performed by the construction which can precisely pickup images of the tooth portions W1 formed periodically and repetitively on the workpiece W, whereby both of the enhancement of the defect detection precision and the shortening of the time required for the image pickup and the inspection can be performed.

Furthermore, according to this embodiment, when the image pickup mechanism 30 picks up images of the tooth portions W1 of the workpiece W, the images are picked up so that at least two tooth portions W1 are contained in each image. The respective tooth portions W1 have different luminosities (brightness), and thus plural images under plural illumination environments which provide different luminosities can be obtained for each tooth portion W1. By inspecting each pickup image, the plural inspecting timings can be set for each tooth portion W1. Accordingly, the time required for the image pickup and the inspection of the workpiece W having the shape portions formed periodically and repetitively thereon can be shortened, and the overlook of a defect can be suppressed.

The present invention is not limited to the above embodiments described above, and various modifications may be made within the scope of the present invention. For example, in each of the embodiments described above, the controller 53 functions as both of the image pickup controller and the inspecting processor. However, the image pickup controller and the inspecting processor may be provided separately from each other. That is, the specific embodiments of the respective parts of the workpiece inspecting apparatus 10 of this embodiment are not limited to the above constructions.

Furthermore, in each of the above embodiments, the workpiece detecting jig 41 is provided. However, the present invention is not limited to this style. For example, the workpiece detecting jig 41 may be omitted, and the proximity sensor 42 may directly detect the tooth portions (shape portions) W1 of the workpiece W.

Still furthermore, in the second embodiment described above, the inclination (tilt) angle θX of the optical axis LL of the illumination light is set to 5° to 20°. However, the present invention is not limited to this style. In short, the inclination (tilt) angle θX may be adjusted to the extent that the unevenness of brightness can be reduced, and it may be arbitrarily adjusted within an acute angle range (0°<θX<90°).

Still furthermore, in each of the above embodiments, the gear wheel is used as the workpiece W. However, the present invention is not limited to this style, and the workpiece W may be a substantially circular workpiece in plan view, for example, parts other than the gear wheel such as an impeller (turbine wheel), a screw or the like. In short, the present invention can be broadly applied to the workpiece inspecting apparatus on which a shape portion such as a projecting portion such as a tooth, a blade (vane) or the like, an inwardly concaved recess portion or the like are periodically and repetitively formed.

What is claimed is:

1. A workpiece inspecting apparatus for rotating a workpiece having a shape portion containing a convex portion and a concave portion which are periodically and repetitively formed on the workpiece and picking up images of the shape portion of the workpiece to inspect the workpiece, comprising:
a workpiece rotating mechanism that outputs reference pulses at a fixed interval while rotating the workpiece at a fixed rotational speed;
an image pickup mechanism that picks up images of the shape portions of the workpiece every image pickup timing based on the reference pulses;
an image pickup controller that synchronizes each of the shape portions of the workpiece with the image pickup timing based on the reference pulses; and
an inspection processor that executes first image processing of taking a difference between a pickup k-th (k represents an integer) image and a pickup (k+1)-th image and first inspecting processing of detecting a defect on the basis of differential data representing the difference, wherein the image pickup mechanism comprises:
a workpiece pulse output mechanism equipped with a rotator that is rotated integrally with the workpiece and has detection target portions arranged at the same angular interval as the shape portions of the workpiece with respect to a rotational center of the rotator, and a proximity sensor that outputs a workpiece pulse every time each of the detection target portions of the rotator is detected; and
a pulse counter that counts an interval between the workpiece pulses on the basis of the reference pulses and achieves a pulse number corresponding to the interval, and the image pickup controller performs image pickup at the image pickup timing based on the reference pulses by using the workpiece pulse as a trigger, and performs image pickup at the image pickup timing based on the reference pulses every time the reference pulses whose number corresponds to the pulse number are output from the image pickup timing.

2. The workpiece inspecting apparatus according to claim 1, wherein the image pickup mechanism picks up the images of the shape portions every fixed period based on the reference pulses so that the shape portions at least two places are contained in each of the pickup images, and has an illuminating device that illuminates light obliquely to the shape portions as references within a predetermined image pickup area when the image pickup mechanism performs image pickup.

3. The workpiece inspecting apparatus according to claim 2, wherein the workpiece is designed to be substantially circular and have the shape portions that are periodically and repetitively formed along a peripheral direction of the workpiece on the workpiece, and the illuminating device illuminates light obliquely to the shape portions as the references within the image pickup area.

4. The workpiece inspecting apparatus according to claim 2, wherein the illuminating device has a transmission type diffuser panel for converting the light to diffusion light and applying the diffusion light to the image pickup area.

5. The workpiece inspecting apparatus according to claim 4, wherein the illuminating device has an optical path portion through which light is passed to the image pickup area of the image pickup mechanism, an optical axis of the optical path portion is oblique to the shape portions as the references within the image pickup area, and the diffuser panel is provided at a light emission side of the optical path portion.

6. The workpiece inspecting apparatus according to claim 5, wherein the optical axis of the optical path portion is oblique to a lens optical axis of the image pickup mechanism.

7. The workpiece inspecting apparatus according to claim 2, wherein a lens optical axis of the image pickup mechanism is offset parallel from a workpiece center passing axis that passes through a rotational center of the workpiece and extends in a radial direction of the workpiece, an illumination center of the illuminating device is disposed at an opposite side to the workpiece center passing axis with respect to the lens optical axis, and the illuminating device is tilted with the illumination center set at a tilting center so that a light emission face of the illuminating device faces a rotational center side of the workpiece W.

8. The workpiece inspecting apparatus according to claim 2, wherein the inspecting processor executes second image processing of obtaining the difference between a pickup image and a pre-stored image of a good product, and executes second inspecting processing of detecting a defect on the basis of data of the difference obtained in the second image processing.

9. The workpiece inspecting apparatus according to claim 8, wherein the inspecting processor determines the workpiece as a good product when no defect is detected in each of the differential data between the pickup k-th image and the pickup (k+1)-th image and the differential data obtained in the other image processing.

10. A workpiece inspecting method for rotating a workpiece having a shape portion containing a convex portion and a concave portion periodically and repetitively formed on the workpiece and picking up images of the shape portions of the workpiece, comprising:
an image pickup step that synchronizes the shape portions of the workpiece with an image pickup timing of an image pickup mechanism for picking up images of the shape portions of the workpiece on the basis of the reference pulses from a workpiece rotating mechanism for outputting reference pulses at a fixed interval while rotating the workpiece at a fixed rotational speed; and
an inspection processing step that executes image processing of achieving the difference between a pickup k (k represents an integer) image and a pickup (k+1)-th image and detects a defect on the basis of the differential data representing the difference, wherein the image pickup step comprises a step for detecting, through a proximity sensor, detection target portions that are provided to a rotator rotating integrally with the workpiece and arranged at the same angular interval as the shape portions of the workpiece with respect to a rotational center of the rotator, a step of counting, on the basis of the reference pulses, an interval between workpiece pulses each of which is output from the proximity sensor every time each of the detection target portions is detected, thereby achieving a pulse number corresponding to the interval, and a step of performing image pickup at the image pickup timing based on the reference pulses by using the workpiece pulse as a trigger and performing image pickup at the image pickup timing based on the reference pulses every time the reference pulses whose number corresponds to the pulse number are output from the image pickup timing.

11. The workpiece inspecting method according to claim 10, wherein when the image pickup mechanism performs image pickup, the image pickup mechanism picks up an image of the shape portions so that the shape portions at least two places are contained in the image, and the respective shape portions are different from each other in luminosity.

* * * * *